(12) United States Patent
Long et al.

(10) Patent No.: US 8,361,066 B2
(45) Date of Patent: Jan. 29, 2013

(54) ELECTRICAL ABLATION DEVICES

(75) Inventors: Gary L. Long, Cincinnati, OH (US); David N. Plescia, Cincinnati, OH (US); Omar J. Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 669 days.

(21) Appl. No.: 12/352,375

(22) Filed: Jan. 12, 2009

(65) Prior Publication Data

US 2010/0179530 A1    Jul. 15, 2010

(51) Int. Cl.
 *A61B 18/14* (2006.01)
(52) U.S. Cl. .......................... 606/41; 606/32
(58) Field of Classification Search ............ 606/31–41
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 2,028,635 A | 1/1936 | Wappler |
| 2,031,682 A | 2/1936 | Wappler et al. |
| 2,113,246 A | 4/1938 | Wappler |
| 2,196,620 A | 4/1940 | Attarian |
| 2,952,206 A | 9/1960 | Becksted |
| 3,435,824 A | 4/1969 | Gamponia |
| 3,470,876 A | 10/1969 | Barchilon |
| 3,595,239 A | 7/1971 | Petersen |
| 3,946,740 A | 3/1976 | Bassett |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |

(Continued)

FOREIGN PATENT DOCUMENTS

| | | |
|---|---|---|
| DE | 3008120 A1 | 9/1980 |
| DE | 4323585 A1 | 1/1995 |

(Continued)

OTHER PUBLICATIONS

International Search Report for PCT/US2010/020465, Jun. 30, 2010 (4 pages).

(Continued)

*Primary Examiner* — Laura Bouchelle

(57) ABSTRACT

An electrical ablation apparatus comprises first and second electrodes. Each electrode comprises a first end configured to couple an energy source and a second end configured to couple to a tissue treatment region. An energy source is coupled to the first and second electrodes. The energy source is configured to deliver a first series of electrical pulses sufficient to induce cell necrosis by irreversible electroporation and a second series of electrical pulses sufficient to induce cell necrosis by thermal heating, through at least one of the first and second electrodes. The first series of electrical pulses is characterized by a first amplitude, a first pulse length, and a first frequency. The second series of electrical pulses is characterized by a second amplitude, a second pulse length, and a second frequency.

14 Claims, 16 Drawing Sheets

U.S. PATENT DOCUMENTS

| | | |
|---|---|---|
| 4,285,344 A | 8/1981 | Marshall |
| 4,311,143 A | 1/1982 | Komiya |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,538,594 A | 9/1985 | Boebel et al. |
| D281,104 S | 10/1985 | Davison |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| D295,894 S | 5/1988 | Sharkany et al. |
| 4,763,669 A | 8/1988 | Jaeger |
| 4,770,188 A | 9/1988 | Chikama |
| 4,823,794 A | 4/1989 | Pierce |
| 4,829,999 A | 5/1989 | Auth |
| 4,867,140 A | 9/1989 | Hovis et al. |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,979,950 A | 12/1990 | Transue et al. |
| 4,984,581 A | 1/1991 | Stice |
| 5,007,917 A | 4/1991 | Evans |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,174,300 A | 12/1992 | Bales et al. |
| 5,176,126 A | 1/1993 | Chikama |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,219,357 A | 6/1993 | Honkanen et al. |
| 5,219,358 A | 6/1993 | Bendel et al. |
| 5,222,965 A | 6/1993 | Haughton |
| 5,234,453 A | 8/1993 | Smith et al. |
| 5,235,964 A | 8/1993 | Abenaim |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,290,302 A | 3/1994 | Pericic |
| 5,295,977 A | 3/1994 | Cohen et al. |
| 5,297,536 A | 3/1994 | Wilk |
| 5,312,351 A | 5/1994 | Gerrone |
| 5,312,416 A | 5/1994 | Spaeth et al. |
| 5,318,589 A | 6/1994 | Lichtman |
| 5,320,636 A | 6/1994 | Slater |
| 5,325,845 A | 7/1994 | Adair |
| 5,330,471 A | 7/1994 | Eggers |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,443,463 A | 8/1995 | Stern et al. |
| 5,445,638 A | 8/1995 | Rydell et al. |
| 5,449,021 A | 9/1995 | Chikama |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,992 A | 3/1996 | Meade et al. |
| 5,503,616 A | 4/1996 | Jones |
| 5,505,686 A | 4/1996 | Willis et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,536,248 A | 7/1996 | Weaver et al. |
| 5,554,151 A | 9/1996 | Hinchliffe |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |

| | | | | | | |
|---|---|---|---|---|---|---|
| 5,618,303 | A | 4/1997 | Marlow et al. | 5,904,702 A | 5/1999 | Ek et al. |
| 5,620,415 | A | 4/1997 | Lucey et al. | 5,908,420 A | 6/1999 | Parins et al. |
| 5,624,399 | A | 4/1997 | Ackerman | 5,911,737 A | 6/1999 | Lee et al. |
| 5,626,578 | A | 5/1997 | Tihon | 5,916,147 A | 6/1999 | Boury |
| 5,628,732 | A | 5/1997 | Antoon, Jr. et al. | 5,921,997 A | 7/1999 | Fogelberg et al. |
| 5,630,782 | A | 5/1997 | Adair | 5,922,008 A | 7/1999 | Gimpelson |
| 5,643,283 | A | 7/1997 | Younker | 5,925,052 A | 7/1999 | Simmons |
| 5,643,294 | A | 7/1997 | Tovey et al. | 5,928,255 A | 7/1999 | Meade et al. |
| 5,645,083 | A | 7/1997 | Essig et al. | 5,944,718 A | 8/1999 | Austin et al. |
| 5,645,565 | A | 7/1997 | Rudd et al. | 5,951,549 A | 9/1999 | Richardson et al. |
| 5,649,372 | A | 7/1997 | Souza | 5,954,720 A | 9/1999 | Wilson et al. |
| 5,653,677 | A | 8/1997 | Okada et al. | 5,954,731 A | 9/1999 | Yoon |
| 5,653,690 | A | 8/1997 | Booth et al. | 5,957,943 A | 9/1999 | Vaitekunas |
| 5,662,663 | A | 9/1997 | Shallman | 5,957,953 A | 9/1999 | DiPoto et al. |
| 5,669,875 | A | 9/1997 | van Eerdenburg | 5,971,995 A | 10/1999 | Rousseau |
| 5,681,324 | A | 10/1997 | Kammerer et al. | 5,976,074 A | 11/1999 | Moriyama |
| 5,681,330 | A | 10/1997 | Hughett et al. | 5,976,075 A | 11/1999 | Beane et al. |
| 5,685,820 | A | 11/1997 | Riek et al. | 5,976,130 A | 11/1999 | McBrayer et al. |
| 5,690,660 | A | 11/1997 | Kauker et al. | 5,980,556 A | 11/1999 | Giordano et al. |
| 5,695,448 | A | 12/1997 | Kimura et al. | 5,984,938 A | 11/1999 | Yoon |
| 5,695,511 | A | 12/1997 | Cano et al. | 5,984,939 A | 11/1999 | Yoon |
| 5,702,438 | A | 12/1997 | Avitall | 5,989,182 A | 11/1999 | Hori et al. |
| 5,709,708 | A | 1/1998 | Thal | 5,993,447 A | 11/1999 | Blewett et al. |
| 5,716,326 | A | 2/1998 | Dannan | 6,001,120 A | 12/1999 | Levin |
| 5,730,740 | A | 3/1998 | Wales et al. | 6,004,269 A | 12/1999 | Crowley et al. |
| 5,735,849 | A | 4/1998 | Baden et al. | 6,004,330 A | 12/1999 | Middleman et al. |
| 5,741,234 | A | 4/1998 | Aboul-Hosn | 6,007,566 A | 12/1999 | Wenstrom, Jr. |
| 5,741,278 | A | 4/1998 | Stevens | 6,010,515 A | 1/2000 | Swain et al. |
| 5,741,285 | A | 4/1998 | McBrayer et al. | 6,017,356 A | 1/2000 | Frederick et al. |
| 5,746,759 | A | 5/1998 | Meade et al. | 6,019,770 A | 2/2000 | Christoudias |
| 5,749,881 | A | 5/1998 | Sackier et al. | 6,024,708 A | 2/2000 | Bales et al. |
| 5,749,889 | A | 5/1998 | Bacich et al. | 6,027,522 A | 2/2000 | Palmer |
| 5,752,951 | A | 5/1998 | Yanik | 6,030,365 A | 2/2000 | Laufer |
| 5,766,167 | A | 6/1998 | Eggers et al. | 6,030,634 A | 2/2000 | Wu et al. |
| 5,766,170 | A | 6/1998 | Eggers | 6,033,399 A | 3/2000 | Gines |
| 5,766,205 | A | 6/1998 | Zvenyatsky et al. | 6,036,685 A | 3/2000 | Mueller |
| 5,769,849 | A | 6/1998 | Eggers | 6,053,927 A | 4/2000 | Hamas |
| 5,779,701 | A | 7/1998 | McBrayer et al. | 6,066,160 A | 5/2000 | Colvin et al. |
| 5,779,716 | A | 7/1998 | Cano et al. | 6,068,629 A | 5/2000 | Haissaguerre et al. |
| 5,779,727 | A | 7/1998 | Orejola | 6,071,233 A | 6/2000 | Ishikawa et al. |
| 5,782,859 | A | 7/1998 | Nicholas et al. | 6,090,108 A | 7/2000 | McBrayer et al. |
| 5,782,866 | A | 7/1998 | Wenstrom, Jr. | 6,096,046 A | 8/2000 | Weiss |
| 5,791,022 | A | 8/1998 | Bohman | 6,102,926 A | 8/2000 | Tartaglia et al. |
| 5,792,113 | A | 8/1998 | Kramer et al. | 6,106,473 A | 8/2000 | Violante et al. |
| 5,792,153 | A | 8/1998 | Swain et al. | 6,109,852 A | 8/2000 | Shahinpoor et al. |
| 5,792,165 | A | 8/1998 | Klieman et al. | 6,110,183 A | 8/2000 | Cope |
| 5,797,835 | A | 8/1998 | Green | 6,139,555 A | 10/2000 | Hart et al. |
| 5,797,928 | A | 8/1998 | Kogasaka | 6,146,391 A | 11/2000 | Cigaina |
| 5,797,939 | A | 8/1998 | Yoon | 6,148,222 A | 11/2000 | Ramsey, III |
| 5,797,941 | A | 8/1998 | Schulze et al. | 6,149,653 A | 11/2000 | Deslauriers |
| 5,803,903 | A | 9/1998 | Athas et al. | 6,149,662 A | 11/2000 | Pugliesi et al. |
| 5,808,665 | A | 9/1998 | Green | 6,159,200 A | 12/2000 | Verdura et al. |
| 5,810,806 | A | 9/1998 | Ritchart et al. | 6,165,184 A | 12/2000 | Verdura et al. |
| 5,810,865 | A | 9/1998 | Koscher et al. | 6,168,605 B1 | 1/2001 | Measamer et al. |
| 5,810,876 | A | 9/1998 | Kelleher | 6,170,130 B1 | 1/2001 | Hamilton et al. |
| 5,810,877 | A | 9/1998 | Roth et al. | 6,179,776 B1 | 1/2001 | Adams et al. |
| 5,813,976 | A | 9/1998 | Filipi et al. | 6,179,837 B1 | 1/2001 | Hooven |
| 5,814,058 | A | 9/1998 | Carlson et al. | 6,190,353 B1 | 2/2001 | Makower et al. |
| 5,817,061 | A | 10/1998 | Goodwin et al. | 6,190,384 B1 | 2/2001 | Ouchi |
| 5,817,107 | A | 10/1998 | Schaller | 6,203,533 B1 | 3/2001 | Ouchi |
| 5,817,119 | A | 10/1998 | Klieman et al. | 6,206,872 B1 | 3/2001 | Lafond et al. |
| 5,819,736 | A | 10/1998 | Avny et al. | 6,206,877 B1 | 3/2001 | Kese et al. |
| 5,824,071 | A | 10/1998 | Nelson et al. | 6,234,958 B1 | 5/2001 | Snoke et al. |
| 5,827,281 | A | 10/1998 | Levin | 6,258,064 B1 | 7/2001 | Smith et al. |
| 5,830,231 | A | 11/1998 | Geiges, Jr. | 6,261,242 B1 | 7/2001 | Roberts et al. |
| 5,833,700 | A | 11/1998 | Fogelberg et al. | 6,264,664 B1 | 7/2001 | Avellanet |
| 5,833,703 | A | 11/1998 | Manushakian | 6,270,497 B1 | 8/2001 | Sekino et al. |
| 5,843,017 | A | 12/1998 | Yoon | 6,270,505 B1 | 8/2001 | Yoshida et al. |
| 5,843,121 | A | 12/1998 | Yoon | 6,277,136 B1 | 8/2001 | Bonutti |
| 5,849,022 | A | 12/1998 | Sakashita et al. | 6,283,963 B1 | 9/2001 | Regula |
| 5,853,374 | A | 12/1998 | Hart et al. | 6,293,909 B1 | 9/2001 | Chu et al. |
| 5,860,913 | A | 1/1999 | Yamaya et al. | 6,293,952 B1 | 9/2001 | Brosens et al. |
| 5,860,995 | A | 1/1999 | Berkelaar | 6,296,630 B1 | 10/2001 | Altman et al. |
| 5,882,331 | A | 3/1999 | Sasaki | 6,322,578 B1 | 11/2001 | Houle et al. |
| 5,882,344 | A | 3/1999 | Stouder, Jr. | 6,326,177 B1 | 12/2001 | Schoenbach et al. |
| 5,893,846 | A | 4/1999 | Bales et al. | 6,350,267 B1 | 2/2002 | Stefanchik |
| 5,893,874 | A | 4/1999 | Bourque et al. | 6,352,503 B1 | 3/2002 | Matsui et al. |
| 5,893,875 | A | 4/1999 | O'Connor et al. | 6,355,035 B1 | 3/2002 | Manushakian |
| 5,899,919 | A | 5/1999 | Eubanks, Jr. et al. | 6,361,534 B1 | 3/2002 | Chen et al. |

| | | |
|---|---|---|
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,391,029 B1 | 5/2002 | Hooven et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,427,089 B1 | 7/2002 | Knowlton |
| 6,431,500 B1 | 8/2002 | Jacobs et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,543,456 B1 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,074 B2 | 8/2003 | Santilli |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,722 B2 | 7/2004 | Cole et al. |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,476 B2 | 6/2005 | Jud et al. |
| 6,916,284 B2 | 7/2005 | Moriyama |
| 6,918,871 B2 | 7/2005 | Schulze |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,942,613 B2 | 9/2005 | Ewers et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,101,371 B2 | 9/2006 | Dycus et al. |

| | | | | | | |
|---|---|---|---|---|---|---|
| 7,101,372 | B2 | 9/2006 | Dycus et al. | 2002/0068945 A1 | 6/2002 | Sixto, Jr. et al. |
| 7,101,373 | B2 | 9/2006 | Dycus et al. | 2002/0078967 A1 | 6/2002 | Sixto, Jr. et al. |
| 7,105,000 | B2 | 9/2006 | McBrayer | 2002/0082516 A1 | 6/2002 | Stefanchik |
| 7,105,005 | B2 | 9/2006 | Blake | 2002/0107530 A1 | 8/2002 | Sauer et al. |
| 7,108,703 | B2 | 9/2006 | Danitz et al. | 2002/0138086 A1 | 9/2002 | Sixto, Jr. et al. |
| 7,112,208 | B2 | 9/2006 | Morris et al. | 2002/0147456 A1 | 10/2002 | Diduch et al. |
| 7,117,703 | B2 | 10/2006 | Kato et al. | 2002/0183591 A1 | 12/2002 | Matsuura et al. |
| 7,118,531 | B2 | 10/2006 | Krill | 2003/0036679 A1 | 2/2003 | Kortenbach et al. |
| 7,118,587 | B2 | 10/2006 | Dycus et al. | 2003/0083681 A1 | 5/2003 | Moutafis et al. |
| 7,128,708 | B2 | 10/2006 | Saadat et al. | 2003/0114732 A1 | 6/2003 | Webler et al. |
| RE39,415 | E | 11/2006 | Bales et al. | 2003/0124009 A1 | 7/2003 | Ravi et al. |
| 7,131,978 | B2 | 11/2006 | Sancoff et al. | 2003/0130564 A1 | 7/2003 | Martone et al. |
| 7,137,980 | B2 | 11/2006 | Buysse et al. | 2003/0130656 A1 | 7/2003 | Levin |
| 7,137,981 | B2 | 11/2006 | Long | 2003/0167062 A1 | 9/2003 | Gambale et al. |
| 7,147,650 | B2 | 12/2006 | Lee | 2003/0171651 A1 | 9/2003 | Page et al. |
| 7,150,097 | B2 | 12/2006 | Sremcich et al. | 2003/0176880 A1 | 9/2003 | Long et al. |
| 7,150,655 | B2 | 12/2006 | Mastrototaro et al. | 2003/0216611 A1 | 11/2003 | Vu |
| 7,152,488 | B2 | 12/2006 | Hedrich et al. | 2003/0216615 A1 | 11/2003 | Ouchi |
| 7,153,321 | B2 | 12/2006 | Andrews | 2003/0225312 A1 | 12/2003 | Suzuki et al. |
| 7,163,525 | B2 | 1/2007 | Franer | 2003/0229269 A1 | 12/2003 | Humphrey |
| 7,172,714 | B2 | 2/2007 | Jacobson | 2003/0229371 A1 | 12/2003 | Whitworth |
| 7,179,254 | B2 | 2/2007 | Pendekanti et al. | 2003/0236549 A1 | 12/2003 | Bonadio et al. |
| 7,188,627 | B2 | 3/2007 | Nelson et al. | 2004/0002683 A1 | 1/2004 | Nicholson et al. |
| 7,195,612 | B2 | 3/2007 | Van Sloten et al. | 2004/0098007 A1 | 5/2004 | Heiss |
| 7,195,631 | B2 | 3/2007 | Dumbauld | 2004/0116948 A1 | 6/2004 | Sixto, Jr. et al. |
| 7,204,820 | B2 | 4/2007 | Akahoshi | 2004/0127940 A1 | 7/2004 | Ginn et al. |
| 7,208,005 | B2 | 4/2007 | Frecker et al. | 2004/0133089 A1 | 7/2004 | Kilcoyne et al. |
| 7,220,227 | B2 | 5/2007 | Sasaki et al. | 2004/0136779 A1 | 7/2004 | Bhaskar |
| 7,223,272 | B2 | 5/2007 | Francese et al. | 2004/0138525 A1 | 7/2004 | Saadat et al. |
| 7,232,445 | B2 | 6/2007 | Kortenbach et al. | 2004/0138529 A1 | 7/2004 | Wiltshire et al. |
| 7,241,290 | B2 | 7/2007 | Doyle et al. | 2004/0138587 A1 | 7/2004 | Lyons, IV |
| 7,244,228 | B2 | 7/2007 | Lubowski | 2004/0161451 A1 | 8/2004 | Pierce et al. |
| 7,250,027 | B2 | 7/2007 | Barry | 2004/0186350 A1 | 9/2004 | Brenneman et al. |
| 7,252,660 | B2 | 8/2007 | Kunz | 2004/0193146 A1 | 9/2004 | Lee et al. |
| 7,255,675 | B2 | 8/2007 | Gertner et al. | 2004/0193186 A1 | 9/2004 | Kortenbach et al. |
| 7,270,663 | B2 | 9/2007 | Nakao | 2004/0193188 A1 | 9/2004 | Francese |
| 7,294,139 | B1 | 11/2007 | Gengler | 2004/0193189 A1 | 9/2004 | Kortenbach et al. |
| 7,306,597 | B2 | 12/2007 | Manzo | 2004/0193200 A1 | 9/2004 | Dworschak et al. |
| 7,308,828 | B2 | 12/2007 | Hashimoto | 2004/0199052 A1 | 10/2004 | Banik et al. |
| 7,320,695 | B2 | 1/2008 | Carroll | 2004/0206859 A1 | 10/2004 | Chong et al. |
| 7,329,256 | B2 | 2/2008 | Johnson et al. | 2004/0210245 A1 | 10/2004 | Erickson et al. |
| 7,329,257 | B2 | 2/2008 | Kanehira et al. | 2004/0215058 A1 | 10/2004 | Zirps et al. |
| 7,329,383 | B2 | 2/2008 | Stinson | 2004/0225186 A1 | 11/2004 | Horne, Jr. et al. |
| 7,344,536 | B1 | 3/2008 | Lunsford et al. | 2004/0230095 A1 | 11/2004 | Stefanchik et al. |
| 7,364,582 | B2 | 4/2008 | Lee | 2004/0230096 A1 | 11/2004 | Stefanchik et al. |
| 7,402,162 | B2 | 7/2008 | Ouchi | 2004/0230097 A1 | 11/2004 | Stefanchik et al. |
| 7,422,590 | B2 | 9/2008 | Kupferschmid et al. | 2004/0249367 A1 | 12/2004 | Saadat et al. |
| 7,488,295 | B2 | 2/2009 | Burbank et al. | 2004/0249394 A1 | 12/2004 | Morris et al. |
| 7,497,867 | B2 | 3/2009 | Lasner et al. | 2005/0004515 A1 | 1/2005 | Hart et al. |
| 7,524,281 | B2 | 4/2009 | Chu et al. | 2005/0033277 A1 | 2/2005 | Clague et al. |
| 7,540,872 | B2 | 6/2009 | Schechter et al. | 2005/0033319 A1 | 2/2005 | Gambale et al. |
| 7,544,203 | B2 | 6/2009 | Chin et al. | 2005/0033333 A1 | 2/2005 | Smith et al. |
| 7,548,040 | B2 | 6/2009 | Lee et al. | 2005/0049616 A1 | 3/2005 | Rivera et al. |
| 7,549,564 | B2 | 6/2009 | Boudreaux | 2005/0065397 A1 | 3/2005 | Saadat et al. |
| 7,559,887 | B2 | 7/2009 | Dannan | 2005/0065517 A1 | 3/2005 | Chin |
| 7,559,916 | B2 | 7/2009 | Smith et al. | 2005/0070754 A1 | 3/2005 | Nobis et al. |
| 7,575,548 | B2 | 8/2009 | Takemoto et al. | 2005/0070763 A1 | 3/2005 | Nobis et al. |
| 7,579,550 | B2 | 8/2009 | Dayton et al. | 2005/0070764 A1 | 3/2005 | Nobis et al. |
| 7,588,557 | B2 | 9/2009 | Nakao | 2005/0080413 A1 | 4/2005 | Canady |
| 7,618,398 | B2 | 11/2009 | Holman et al. | 2005/0090837 A1 | 4/2005 | Sixto, Jr. et al. |
| 7,674,259 | B2 | 3/2010 | Shadduck | 2005/0090838 A1 | 4/2005 | Sixto, Jr. et al. |
| 7,713,189 | B2 | 5/2010 | Hanke | 2005/0101837 A1 | 5/2005 | Kalloo et al. |
| 7,744,615 | B2 | 6/2010 | Couture | 2005/0101838 A1 | 5/2005 | Camillocci et al. |
| 7,758,577 | B2 | 7/2010 | Nobis et al. | 2005/0107664 A1 | 5/2005 | Kalloo et al. |
| 7,780,691 | B2 | 8/2010 | Stefanchik | 2005/0110881 A1 | 5/2005 | Glukhovsky et al. |
| 7,794,409 | B2 | 9/2010 | Damarati | 2005/0113847 A1 | 5/2005 | Gadberry et al. |
| 7,828,186 | B2 | 11/2010 | Wales | 2005/0119613 A1 | 6/2005 | Moenning et al. |
| 7,846,171 | B2 | 12/2010 | Kullas et al. | 2005/0124855 A1 | 6/2005 | Jaffe et al. |
| 7,892,220 | B2 | 2/2011 | Faller et al. | 2005/0125010 A1 | 6/2005 | Smith et al. |
| 7,909,809 | B2 | 3/2011 | Scopton et al. | 2005/0131279 A1 | 6/2005 | Boulais et al. |
| 7,914,513 | B2 | 3/2011 | Voorhees, Jr. | 2005/0131457 A1 | 6/2005 | Douglas et al. |
| 7,945,332 | B2 | 5/2011 | Schechter | 2005/0137454 A1 | 6/2005 | Saadat et al. |
| 7,988,685 | B2 | 8/2011 | Ziaie et al. | 2005/0143690 A1 | 6/2005 | High |
| 8,075,587 | B2 | 12/2011 | Ginn | 2005/0143774 A1 | 6/2005 | Polo |
| 2001/0049497 A1 | | 12/2001 | Kalloo et al. | 2005/0149087 A1 | 7/2005 | Ahlberg et al. |
| 2002/0022857 A1 | | 2/2002 | Goldsteen et al. | 2005/0149096 A1 | 7/2005 | Hilal et al. |
| 2002/0023353 A1 | | 2/2002 | Ting-Kung | 2005/0159648 A1 | 7/2005 | Freed |
| 2002/0029055 A1 | | 3/2002 | Bonutti | 2005/0165272 A1 | 7/2005 | Okada et al. |
| 2002/0042562 A1 | | 4/2002 | Meron et al. | 2005/0165378 A1 | 7/2005 | Heinrich et al. |

| | | | | | | |
|---|---|---|---|---|---|---|
| 2005/0165411 A1 | 7/2005 | Orban, III | | 2006/0258955 A1 | 11/2006 | Hoffman et al. |
| 2005/0165429 A1 | 7/2005 | Douglas et al. | | 2006/0259010 A1 | 11/2006 | Stefanchik et al. |
| 2005/0192598 A1 | 9/2005 | Johnson et al. | | 2006/0264752 A1 | 11/2006 | Rubinsky et al. |
| 2005/0192602 A1 | 9/2005 | Manzo | | 2006/0264930 A1 | 11/2006 | Nishimura |
| 2005/0209624 A1 | 9/2005 | Vijay | | 2006/0271102 A1 | 11/2006 | Bosshard et al. |
| 2005/0215858 A1 | 9/2005 | Vail, III | | 2006/0276835 A1 | 12/2006 | Uchida |
| 2005/0216050 A1 | 9/2005 | Sepetka et al. | | 2006/0285732 A1 | 12/2006 | Horn et al. |
| 2005/0228406 A1 | 10/2005 | Bose | | 2006/0287644 A1 | 12/2006 | Inganas et al. |
| 2005/0234297 A1 | 10/2005 | Devierre et al. | | 2006/0287666 A1 | 12/2006 | Saadat et al. |
| 2005/0250990 A1 | 11/2005 | Le et al. | | 2007/0002135 A1 | 1/2007 | Glukhovsky |
| 2005/0251176 A1 | 11/2005 | Swanstrom et al. | | 2007/0005019 A1 | 1/2007 | Okishige |
| 2005/0261674 A1 | 11/2005 | Nobis et al. | | 2007/0010801 A1 | 1/2007 | Chen et al. |
| 2005/0267492 A1 | 12/2005 | Poncet et al. | | 2007/0015965 A1 | 1/2007 | Cox et al. |
| 2005/0272975 A1 | 12/2005 | McWeeney et al. | | 2007/0016255 A1 | 1/2007 | Korb et al. |
| 2005/0272977 A1 | 12/2005 | Saadat et al. | | 2007/0032700 A1 | 2/2007 | Fowler et al. |
| 2005/0273084 A1 | 12/2005 | Hinman et al. | | 2007/0032701 A1 | 2/2007 | Fowler et al. |
| 2005/0277945 A1 | 12/2005 | Saadat et al. | | 2007/0043345 A1* | 2/2007 | Davalos et al. ............. 606/32 |
| 2005/0277951 A1 | 12/2005 | Smith et al. | | 2007/0049800 A1 | 3/2007 | Boulais |
| 2005/0277952 A1 | 12/2005 | Arp et al. | | 2007/0051375 A1 | 3/2007 | Milliman |
| 2005/0277954 A1 | 12/2005 | Smith et al. | | 2007/0060880 A1 | 3/2007 | Gregorich et al. |
| 2005/0277955 A1 | 12/2005 | Palmer et al. | | 2007/0079924 A1 | 4/2007 | Saadat et al. |
| 2005/0277956 A1 | 12/2005 | Francese et al. | | 2007/0100376 A1 | 5/2007 | Mikkaichi et al. |
| 2005/0277957 A1 | 12/2005 | Kuhns et al. | | 2007/0106118 A1 | 5/2007 | Moriyama |
| 2005/0283118 A1 | 12/2005 | Uth et al. | | 2007/0112331 A1 | 5/2007 | Weber et al. |
| 2005/0288555 A1 | 12/2005 | Binmoeller | | 2007/0112342 A1 | 5/2007 | Pearson et al. |
| 2006/0004406 A1 | 1/2006 | Wehrstein et al. | | 2007/0112383 A1 | 5/2007 | Conlon et al. |
| 2006/0004409 A1 | 1/2006 | Nobis et al. | | 2007/0112384 A1 | 5/2007 | Conlon et al. |
| 2006/0004410 A1 | 1/2006 | Nobis et al. | | 2007/0112385 A1 | 5/2007 | Conlon |
| 2006/0015009 A1 | 1/2006 | Jaffe et al. | | 2007/0112425 A1 | 5/2007 | Schaller et al. |
| 2006/0020167 A1 | 1/2006 | Sitzmann | | 2007/0118115 A1 | 5/2007 | Artale et al. |
| 2006/0020247 A1 | 1/2006 | Kagan et al. | | 2007/0123840 A1 | 5/2007 | Cox |
| 2006/0025654 A1 | 2/2006 | Suzuki et al. | | 2007/0129719 A1 | 6/2007 | Kendale et al. |
| 2006/0025819 A1 | 2/2006 | Nobis et al. | | 2007/0129760 A1 | 6/2007 | Demarais et al. |
| 2006/0036267 A1 | 2/2006 | Saadat et al. | | 2007/0135709 A1 | 6/2007 | Rioux et al. |
| 2006/0041188 A1 | 2/2006 | Dirusso et al. | | 2007/0135803 A1 | 6/2007 | Belson |
| 2006/0058582 A1 | 3/2006 | Maahs et al. | | 2007/0142780 A1 | 6/2007 | Van Lue |
| 2006/0058776 A1 | 3/2006 | Bilsbury | | 2007/0154460 A1 | 7/2007 | Kraft et al. |
| 2006/0069425 A1 | 3/2006 | Hillis et al. | | 2007/0156028 A1 | 7/2007 | Van Lue et al. |
| 2006/0079890 A1 | 4/2006 | Guerra | | 2007/0156127 A1 | 7/2007 | Rioux et al. |
| 2006/0089528 A1 | 4/2006 | Tartaglia et al. | | 2007/0162101 A1 | 7/2007 | Burgermeister et al. |
| 2006/0095031 A1 | 5/2006 | Ormsby | | 2007/0173869 A1 | 7/2007 | Gannoe et al. |
| 2006/0095060 A1 | 5/2006 | Mayenberger et al. | | 2007/0173870 A2 | 7/2007 | Zacharias |
| 2006/0106423 A1 | 5/2006 | Weisel et al. | | 2007/0173872 A1 | 7/2007 | Neuenfeldt |
| 2006/0111209 A1 | 5/2006 | Hinman et al. | | 2007/0179525 A1 | 8/2007 | Frecker et al. |
| 2006/0111704 A1 | 5/2006 | Brenneman et al. | | 2007/0179530 A1 | 8/2007 | Tieu et al. |
| 2006/0129166 A1 | 6/2006 | Lavelle | | 2007/0198057 A1 | 8/2007 | Gelbart et al. |
| 2006/0135971 A1 | 6/2006 | Swanstrom et al. | | 2007/0203487 A1 | 8/2007 | Sugita |
| 2006/0135984 A1 | 6/2006 | Kramer et al. | | 2007/0208336 A1 | 9/2007 | Kim et al. |
| 2006/0142644 A1 | 6/2006 | Mulac et al. | | 2007/0208364 A1 | 9/2007 | Smith et al. |
| 2006/0142790 A1 | 6/2006 | Gertner | | 2007/0213754 A1 | 9/2007 | Mikkaichi et al. |
| 2006/0149131 A1 | 7/2006 | Or | | 2007/0225554 A1 | 9/2007 | Maseda et al. |
| 2006/0149132 A1 | 7/2006 | Iddan | | 2007/0233040 A1 | 10/2007 | Macnamara et al. |
| 2006/0149135 A1 | 7/2006 | Paz | | 2007/0244358 A1 | 10/2007 | Lee |
| 2006/0161190 A1 | 7/2006 | Gadberry et al. | | 2007/0250038 A1 | 10/2007 | Boulais |
| 2006/0167416 A1 | 7/2006 | Mathis et al. | | 2007/0250057 A1 | 10/2007 | Nobis et al. |
| 2006/0167482 A1 | 7/2006 | Swain et al. | | 2007/0255096 A1 | 11/2007 | Stefanchik et al. |
| 2006/0178560 A1 | 8/2006 | Saadat et al. | | 2007/0255100 A1 | 11/2007 | Barlow et al. |
| 2006/0183975 A1 | 8/2006 | Saadat et al. | | 2007/0255273 A1 | 11/2007 | Fernandez et al. |
| 2006/0189844 A1 | 8/2006 | Tien | | 2007/0255303 A1 | 11/2007 | Bakos et al. |
| 2006/0189845 A1 | 8/2006 | Maahs et al. | | 2007/0255306 A1 | 11/2007 | Conlon et al. |
| 2006/0190027 A1 | 8/2006 | Downey | | 2007/0260112 A1 | 11/2007 | Rahmani |
| 2006/0195084 A1 | 8/2006 | Slater | | 2007/0260117 A1 | 11/2007 | Zwolinski et al. |
| 2006/0200005 A1 | 9/2006 | Bjork et al. | | 2007/0260121 A1 | 11/2007 | Bakos et al. |
| 2006/0200169 A1 | 9/2006 | Sniffin | | 2007/0260273 A1 | 11/2007 | Cropper et al. |
| 2006/0200170 A1 | 9/2006 | Aranyi | | 2007/0270629 A1 | 11/2007 | Charles |
| 2006/0200199 A1 | 9/2006 | Bonutti et al. | | 2007/0270889 A1 | 11/2007 | Conlon et al. |
| 2006/0217697 A1 | 9/2006 | Lau et al. | | 2007/0270907 A1 | 11/2007 | Stokes et al. |
| 2006/0217742 A1 | 9/2006 | Messerly et al. | | 2007/0282371 A1 | 12/2007 | Lee et al. |
| 2006/0217743 A1 | 9/2006 | Messerly et al. | | 2007/0293727 A1 | 12/2007 | Goldfarb et al. |
| 2006/0229639 A1 | 10/2006 | Whitfield | | 2008/0004650 A1 | 1/2008 | George |
| 2006/0229640 A1 | 10/2006 | Whitfield | | 2008/0015409 A1 | 1/2008 | Barlow et al. |
| 2006/0237022 A1 | 10/2006 | Chen et al. | | 2008/0015552 A1 | 1/2008 | Doyle et al. |
| 2006/0237023 A1 | 10/2006 | Cox et al. | | 2008/0021416 A1 | 1/2008 | Arai et al. |
| 2006/0253004 A1 | 11/2006 | Frisch et al. | | 2008/0022927 A1 | 1/2008 | Zhang et al. |
| 2006/0253039 A1 | 11/2006 | McKenna et al. | | 2008/0027387 A1 | 1/2008 | Grabinsky |
| 2006/0258907 A1 | 11/2006 | Stefanchik et al. | | 2008/0051735 A1 | 2/2008 | Measamer et al. |
| 2006/0258908 A1 | 11/2006 | Stefanchik et al. | | 2008/0058586 A1 | 3/2008 | Karpiel |
| 2006/0258910 A1 | 11/2006 | Stefanchik et al. | | 2008/0071264 A1* | 3/2008 | Azure ............................. 606/41 |
| 2006/0258954 A1 | 11/2006 | Timberlake et al. | | 2008/0086172 A1 | 4/2008 | Martin et al. |

| | | |
|---|---|---|
| 2008/0097159 A1 | 4/2008 | Ishiguro |
| 2008/0097483 A1 | 4/2008 | Ortiz et al. |
| 2008/0103527 A1 | 5/2008 | Martin et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0243106 A1 | 10/2008 | Coe et al. |
| 2008/0249567 A1 | 10/2008 | Kaplan |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287983 A1 | 11/2008 | Smith et al. |
| 2008/0300547 A1 | 12/2008 | Bakos |
| 2008/0312496 A1 | 12/2008 | Zwolinski |
| 2008/0312506 A1 | 12/2008 | Spivey et al. |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0078736 A1 | 3/2009 | Van Lue |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0216248 A1 | 8/2009 | Uenohara et al. |
| 2009/0227828 A1 | 9/2009 | Swain et al. |
| 2009/0248055 A1 | 10/2009 | Spivey et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0179510 A1 | 7/2010 | Fox et al. |
| 2010/0261994 A1 | 10/2010 | Davalos et al. |
| 2010/0331758 A1 | 12/2010 | Davalos et al. |
| 2011/0106221 A1 | 5/2011 | Neal, II et al. |
| 2011/0190659 A1 | 8/2011 | Long et al. |
| 2011/0190764 A1 | 8/2011 | Long et al. |
| 2011/0245619 A1 | 10/2011 | Holcomb |
| 2011/0306971 A1 | 12/2011 | Long |
| 2012/0004502 A1 | 1/2012 | Weitzner et al. |

FOREIGN PATENT DOCUMENTS

| | | |
|---|---|---|
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 1493397 B1 | 9/2011 |
| FR | 2731610 A1 | 9/1996 |
| GB | 2335860 A | 10/1999 |
| GB | 2403909 A | 1/2005 |
| JP | 63309252 A | 12/1988 |
| JP | 4038960 A | 2/1992 |
| JP | 2000245683 A | 9/2000 |

| | | | |
|---|---|---|---|
| JP | 2002-369791 A | 12/2002 | |
| JP | 2003-088494 A | 3/2003 | |
| JP | 2003-235852 A | 8/2003 | |
| JP | 2004-33525 A | 2/2004 | |
| JP | 2004-065745 A | 3/2004 | |
| JP | 2005-121947 A | 5/2005 | |
| JP | 2005-261514 A | 9/2005 | |
| JP | 2006297005 A | 11/2006 | |
| NL | 1021295 C2 | 2/2004 | |
| SU | 194230 | 5/1967 | |
| SU | 980703 | 12/1982 | |
| WO | WO 84/01707 A1 | 5/1984 | |
| WO | WO 92/13494 A1 | 8/1992 | |
| WO | WO 93/10850 A1 | 6/1993 | |
| WO | WO 93/20760 A1 | 10/1993 | |
| WO | WO 93/20765 A1 | 10/1993 | |
| WO | WO 95/09666 A1 | 4/1995 | |
| WO | WO 96/22056 A1 | 7/1996 | |
| WO | WO 96/27331 A1 | 9/1996 | |
| WO | WO 96/39946 A1 | 12/1996 | |
| WO | WO 97/12557 A1 | 4/1997 | |
| WO | WO 99/00060 A1 | 1/1999 | |
| WO | WO 99/09919 A1 | 3/1999 | |
| WO | WO 99/17661 A1 | 4/1999 | |
| WO | WO 99/30622 A2 | 6/1999 | |
| WO | WO 00/35358 A1 | 6/2000 | |
| WO | WO 01/26708 A1 | 4/2001 | |
| WO | WO 01/58360 A2 | 8/2001 | |
| WO | WO 02/11621 A1 | 2/2002 | |
| WO | WO 02/34122 A2 | 5/2002 | |
| WO | WO 02/094082 A2 | 11/2002 | |
| WO | WO 03/045260 A1 | 6/2003 | |
| WO | WO 03/059412 A2 | 7/2003 | |
| WO | WO 03/078721 A2 | 9/2003 | |
| WO | WO 03/081761 A2 | 10/2003 | |
| WO | WO 03/082129 A2 | 10/2003 | |
| WO | WO 2004/006789 A1 | 1/2004 | |
| WO | WO 2004/028613 A2 | 4/2004 | |
| WO | WO 2004/037123 A1 | 5/2004 | |
| WO | WO 2004/037149 A1 | 5/2004 | |
| WO | WO 2004/052221 A1 | 6/2004 | |
| WO | WO 2004/086984 A1 | 10/2004 | |
| WO | WO 2005/009211 A2 | 2/2005 | |
| WO | WO 2005/018467 A2 | 3/2005 | |
| WO | WO 2005/037088 A2 | 4/2005 | |
| WO | WO 2005/065284 A2 | 7/2005 | |
| WO | WO 2005/112810 A2 | 12/2005 | |
| WO | WO 2005/120363 A2 | 12/2005 | |
| WO | WO 2006/007399 A1 | 1/2006 | |
| WO | WO 2006/012630 A2 | 2/2006 | |
| WO | WO 2006/040109 A1 | 4/2006 | |
| WO | WO 2006/041881 A2 | 4/2006 | |
| WO | WO 2006/060405 A2 | 6/2006 | |
| WO | WO 2006/110733 A2 | 10/2006 | |
| WO | WO 2006/113216 A2 | 10/2006 | |
| WO | WO 2007/013059 A2 | 2/2007 | |
| WO | WO 2007/048085 A2 | 4/2007 | |
| WO | WO 2007/063550 A2 | 6/2007 | |
| WO | WO 2007/100067 A1 | 9/2007 | |
| WO | WO 2007/109171 A2 | 9/2007 | |
| WO | WO 2008/033356 A2 | 3/2008 | |
| WO | WO 2008/076337 A1 | 6/2008 | |
| WO | WO 2008/076800 A2 | 6/2008 | |
| WO | WO 2008/079440 A2 | 7/2008 | |
| WO | WO 2008/101075 A2 | 8/2008 | |
| WO | WO 2008/102154 A2 | 8/2008 | |
| WO | WO 2008/108863 A2 | 9/2008 | |
| WO | WO 2008/151237 A1 | 12/2008 | |
| WO | WO 2009/027065 A1 | 3/2009 | |
| WO | WO 2009/032623 A2 | 3/2009 | |
| WO | WO 2009/121017 A1 | 10/2009 | |
| WO | WO 2010/027688 A1 | 3/2010 | |
| WO | WO 2010/080974 A1 | 7/2010 | |

OTHER PUBLICATIONS

D. Wilhelm et al., "An Innovative, Safe and Sterile Sigmoid Access (ISSA) for Notes," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 11/897,676, filed Aug. 31, 2007.

Michael S. Kavic, M.D., "Natural Orifice Translumenal Endoscopic Surgery: "NOTES"", JSLS, vol. 10, pp. 133-134 (2006).

Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis col. Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview& navRelId=1000.1003&method=D . . . , accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200.

U.S. Appl. No. 12/019,461, filed Jan. 24, 2008.
U.S. Appl. No. 12/045,318, filed Mar. 10, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.

U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
Written Opinion for PCT/US2010/020465, Jun. 30, 2010 (10 pages).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).

Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/218,221, filed Aug. 25, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818 filed Mar. 15, 2012.
U.S. Appl. No. 13/425,103, filed Mar. 20, 2012.

* cited by examiner

ELECTRICAL ABLATION DEVICES

BACKGROUND

Electrical ablation therapy has been employed in medicine for the treatment of undesirable tissue such as diseased tissue, cancer, malignant and benign tumors, masses, lesions, and other abnormal tissue growths. While conventional apparatuses, systems, and methods for the electrical ablation of undesirable tissue are effective, one drawback with conventional electrical ablation treatment is the resulting permanent damage that may occur to the healthy tissue surrounding the abnormal tissue due primarily to the detrimental thermal effects resulting from exposing the tissue to thermal energy generated by the electrical ablation device. This may be particularly true when exposing the tissue to electric potentials sufficient to cause cell necrosis using high temperature thermal therapies including focused ultrasound ablation, radiofrequency (RF) ablation, or interstitial laser coagulation. Other techniques for tissue ablation include chemical ablation, in which chemical agents are injected into the undesirable tissue to cause ablation as well as surgical excision, cryotherapy, radiation, photodynamic therapy, Moh's micrographic surgery, topical treatments with 5-fluorouracil, laser ablation. Other drawbacks of conventional thermal, chemical, and other ablation therapy are cost, length of recovery, and the extraordinary pain inflicted on the patient.

Conventional thermal, chemical, and other ablation techniques have been employed for the treatment of a variety of undesirable tissue. Thermal and chemical ablation techniques have been used for the treatment of varicose veins resulting from reflux disease of the greater saphenous vein (GSV), in which the varicose vein is stripped and then is exposed to either chemical or thermal ablation. Other techniques for the treatment of undesirable tissue are more radical. Prostate cancer, for example, may be removed using a prostatectomy, in which the entire or part of prostate gland and surrounding lymph nodes are surgically removed. Like most other forms of cancer, radiation therapy may be used in conjunction with or as an alternate method for the treatment of prostate cancer. Another thermal ablation technique for the treatment of prostate cancer is RF interstitial tumor ablation (RITA) via transrectal ultrasound guidance. While these conventional methods for the treatment of prostate cancer are effective, they are not preferred by many surgeons and may result in detrimental thermal effects to healthy tissue surrounding the prostate. Similar thermal ablation techniques may be used for the treatment of basal cell carcinoma (BCC) tissue, a slowly growing cutaneous malignancy derived from the rapidly proliferating basal layer of the epidermis. BCC tissue in tumors ranging in size from about 5 mm to about 40 mm may be thermally ablated with a pulsed carbon dioxide laser. Nevertheless, carbon dioxide laser ablation is a thermal treatment method and may cause permanent damage to healthy tissue surrounding the BCC tissue. Furthermore, this technique requires costly capital investment in carbon dioxide laser equipment. Undesirable tissue growing inside a body lumen such as the esophagus, large bowel, or in cavities formed in solid tissue such as the breast, for example, can be difficult to destroy using conventional ablation techniques. Surgical removal of undesirable tissue, such as a malignant or benign tumor, from the breast is likely to leave a cavity. Surgical resection of residual intralumenal tissue may remove only a portion of the undesirable tissue cells within a certain margin of healthy tissue. Accordingly, some undesirable tissue is likely to remain within the wall of the cavity due to the limitation of conventional ablation instrument configurations, which may be effective for treating line-of-sight regions of tissue, but may be less effective for treating the residual undesirable tissue.

Accordingly, there remains a need for improved electrical ablation apparatuses, systems, and methods for the treatment of undesirable tissue found in diseased tissue, cancer, malignant and benign tumors, masses, lesions, and other abnormal tissue growths. There remains a need for minimally invasive treatment of undesirable tissue through the use of irreversible electroporation (IRE) ablation techniques without causing the detrimental thermal effects of conventional thermal ablation techniques.

FIGURES

The novel features of the various described embodiments are set forth with particularity in the appended claims. The various embodiments, however, both as to organization and methods of operation, together with advantages thereof, may be understood in accordance with the following description taken in conjunction with the accompanying drawings as follows.

FIG. 1 illustrates one embodiment of an electrical ablation system.

FIGS. 2A-D illustrate one embodiment of the electrical ablation device in various phases of deployment.

Figure 6:
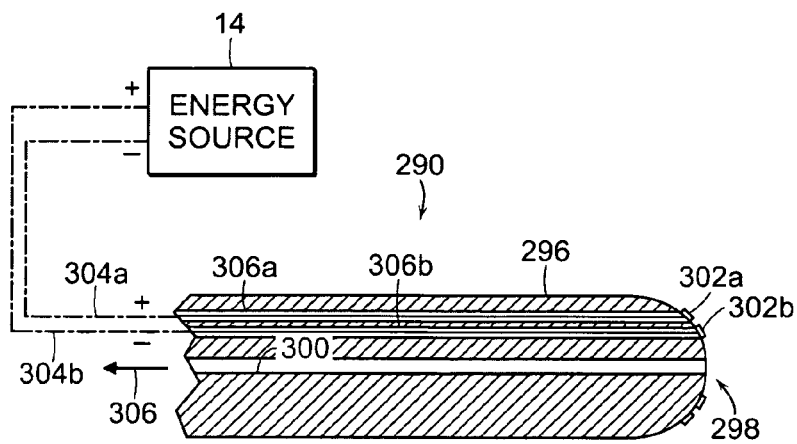
Figure 7:
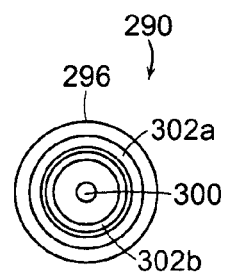
Figure 8:
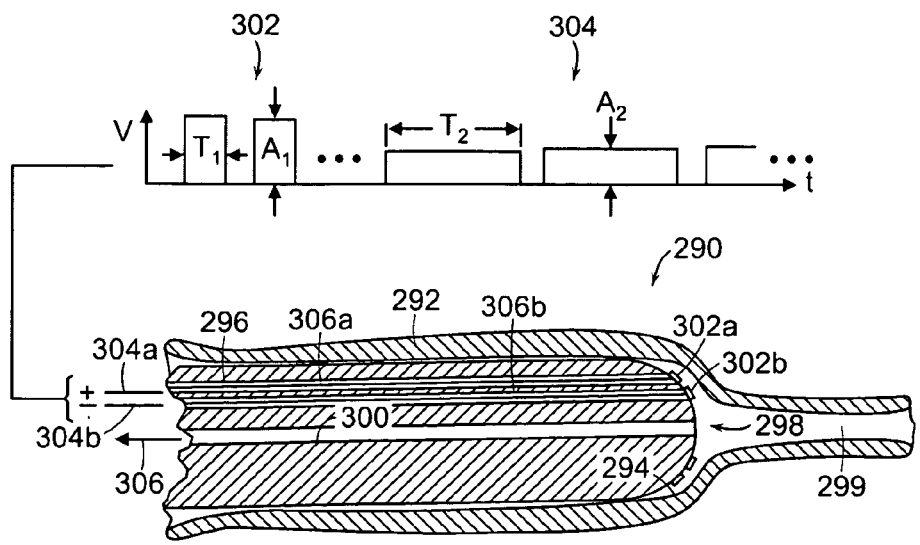

FIGS. 6, 7, and 8 illustrate one embodiment of an electrical ablation device to treat undesirable tissue within body lumen using electrical energy, where FIG. 6 illustrates a sectioned view of one embodiment of an electrical ablation device, FIG. 7 illustrates an end view of one embodiment of the electrical ablation device shown in FIG. 6, and FIG. 8 illustrates a cross-sectional view of one embodiment of the electrical ablation device shown in FIG. 6.

Figure 9:
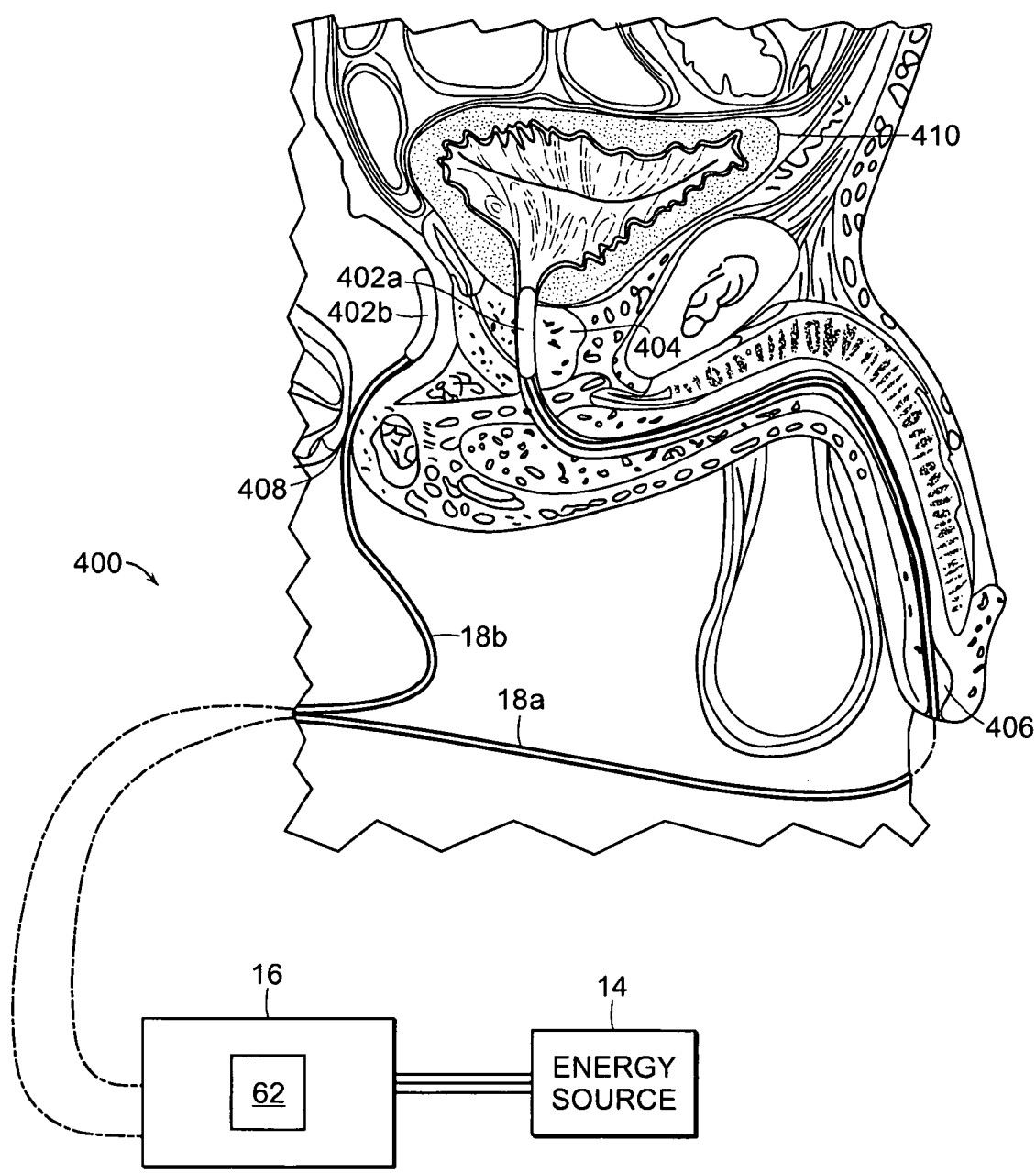

FIG. 9 illustrates one embodiment of an electrical ablation system in use to treat non-metastatic prostate cancer in a patient.

Figure 10:
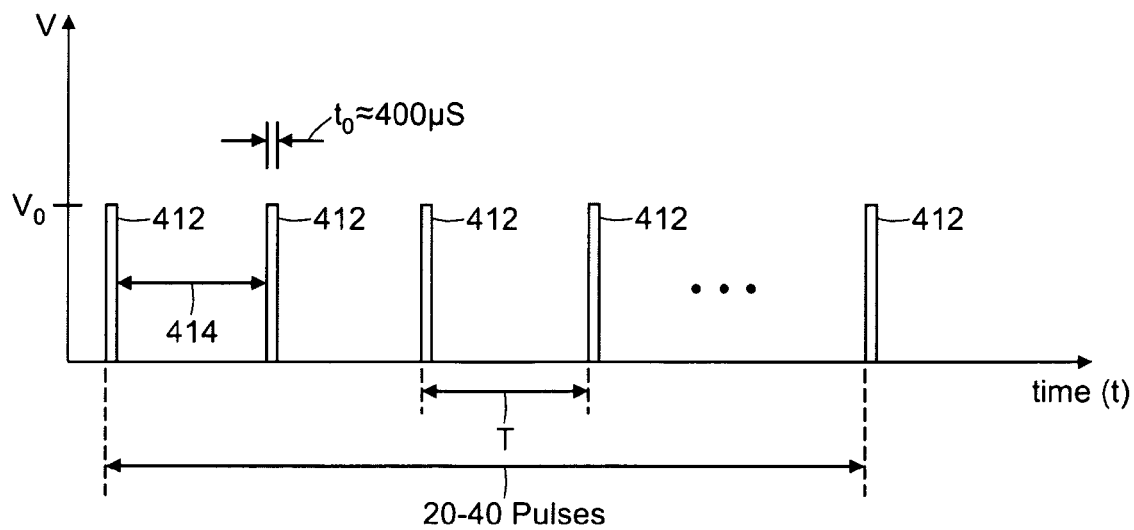

FIG. 10 is a graphical representation of a series of electrical pulses that may be applied to undesirable tissue to induce irreversible electroporation suitable to ablate non-metastatic cancer of the prostrate as described in FIG. 9.

Figure 1:
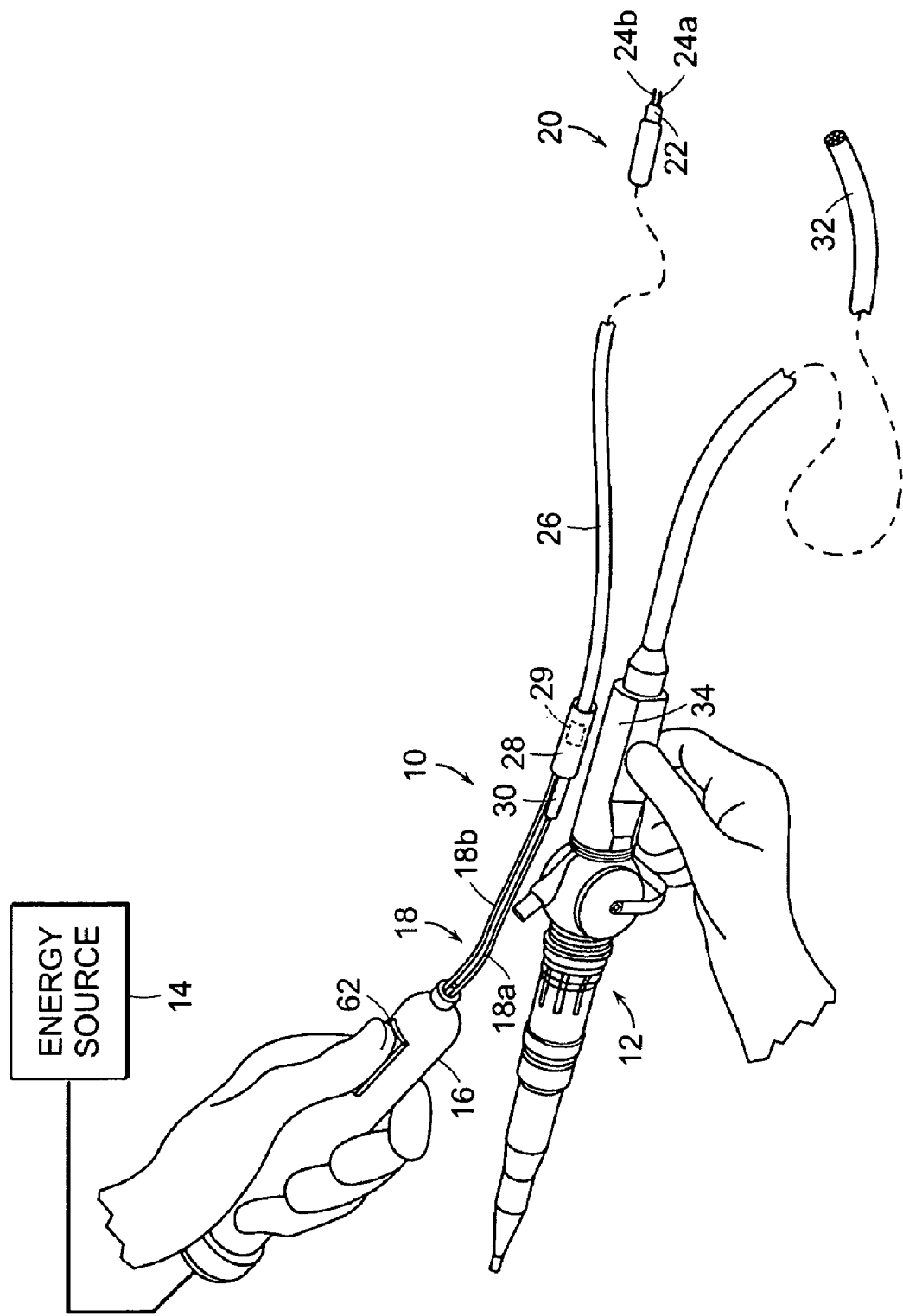
Figure 11:
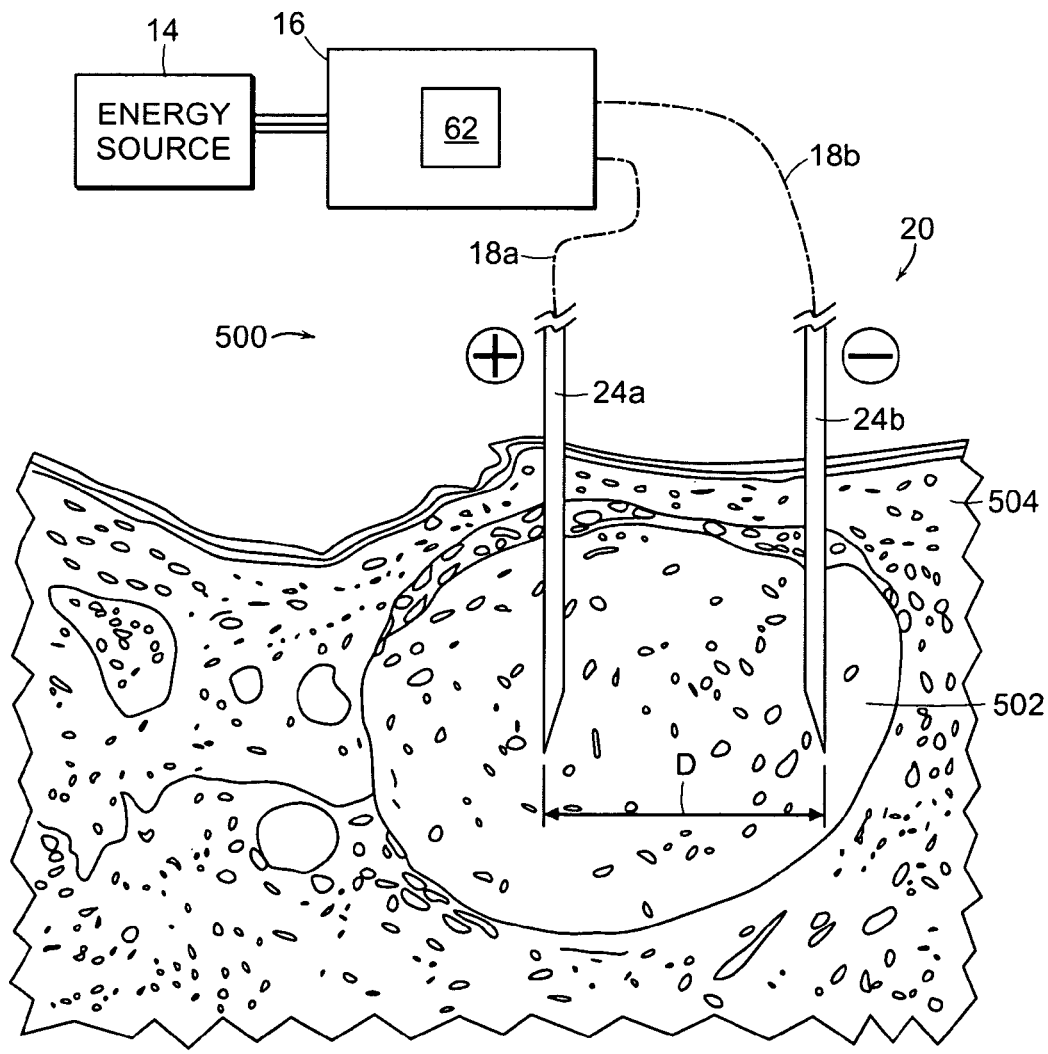

FIG. 11 illustrates one embodiment of the electrical ablation system described FIG. 1 in use to treat basal cell carcinoma (BCC) tissue.

Figure 12:
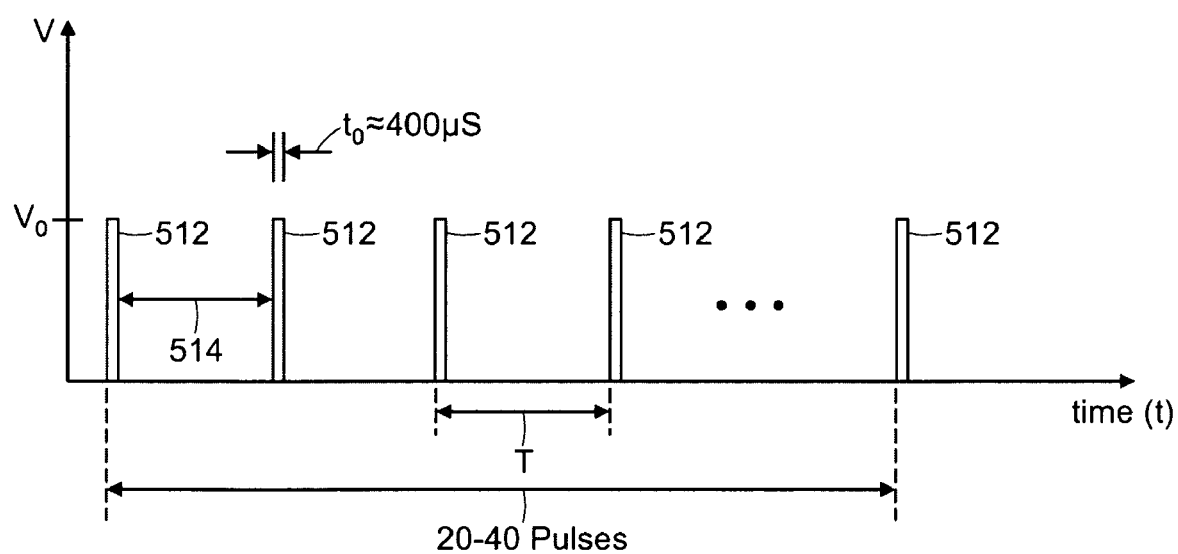

FIG. 12 is a graphical representation of a series of electrical pulses for treating basal cell carcinoma (BCC) tissue as shown in FIG. 11 with irreversible electroporation energy.

Figure 13A:
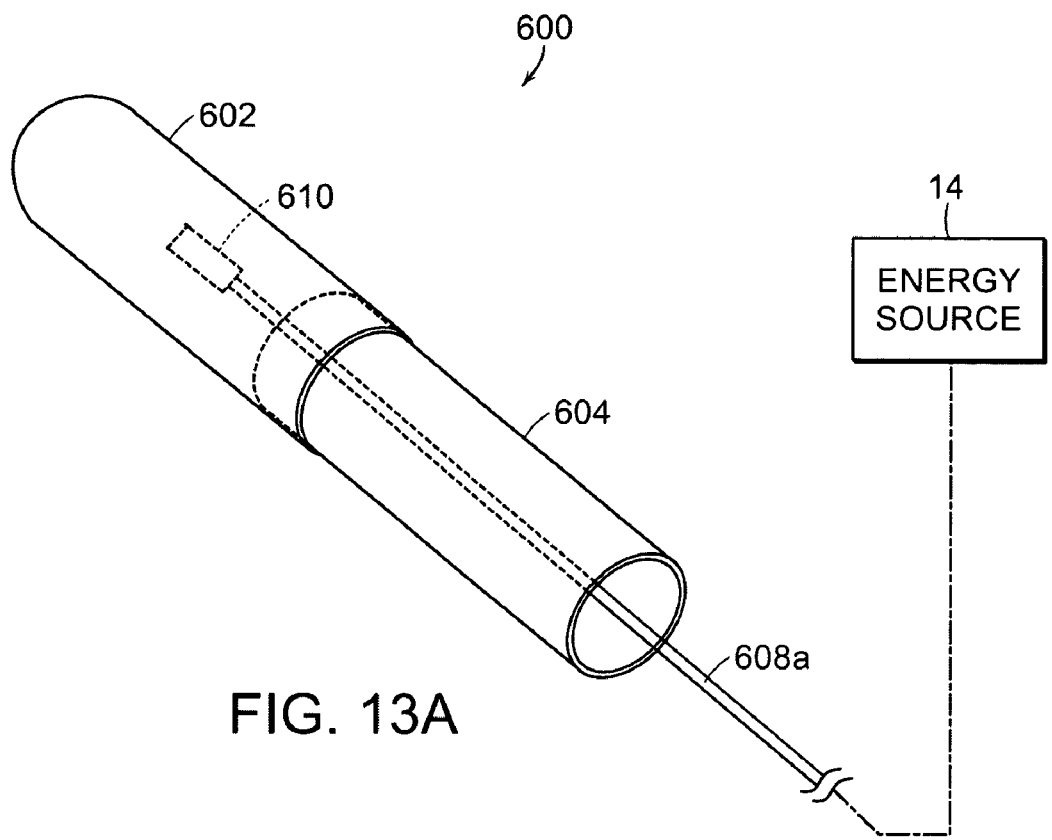

FIG. 13A illustrates one embodiment of an electrical ablation device, in a collapsed state, the device having a configuration suitable for the treatment of abnormal tissue located in a lumen, abscess, void, or cavity.

Figure 13B:
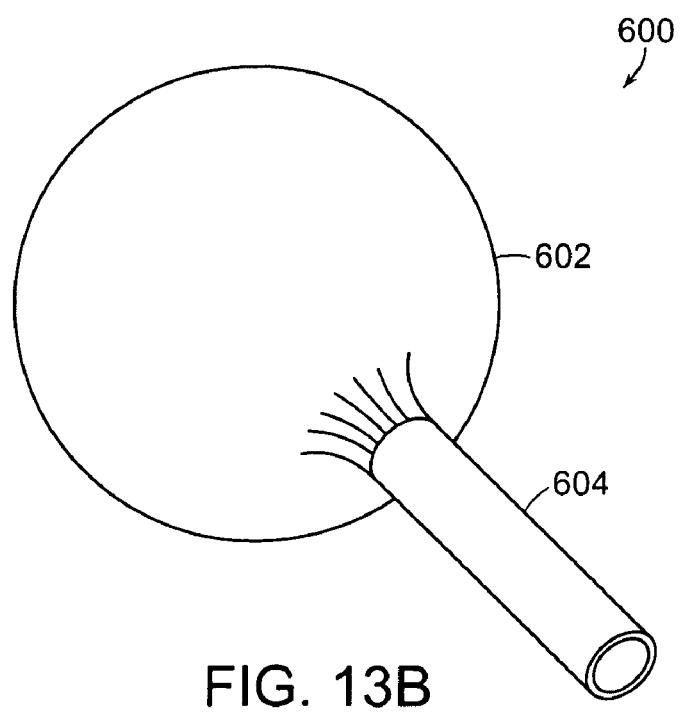

FIG. 13B illustrates one embodiment of the electrical ablation device shown in FIG. 13A, in an inflated state, the device having a configuration suitable for the treatment of abnormal tissue located in a lumen, abscess, void, or cavity.

Figure 14:
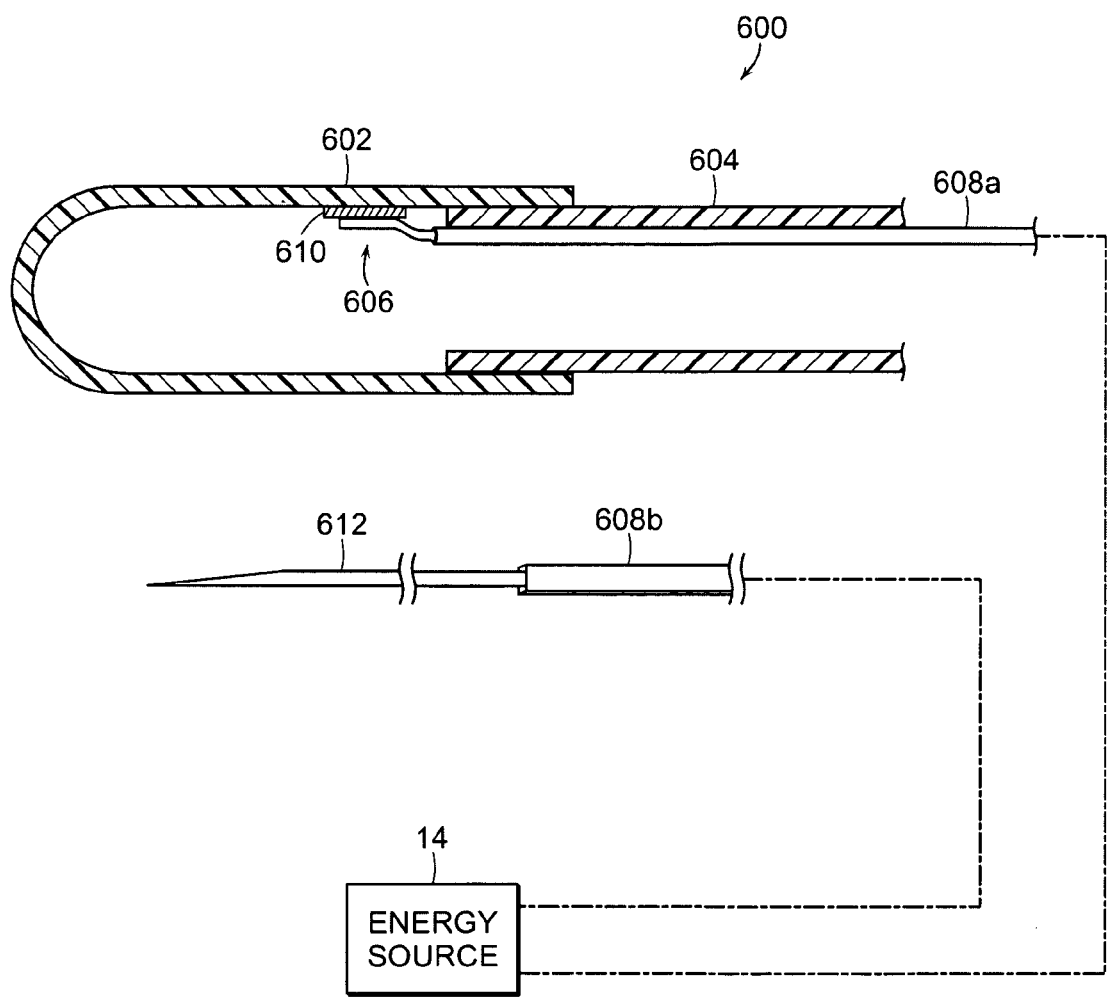

FIG. 14 is a cross-sectional view of the electrical ablation device showing a cross-sectional view of the conductive elastomer electrode and the non-conductive catheter shown in FIGS. 13A and 13B.

Figure 15:
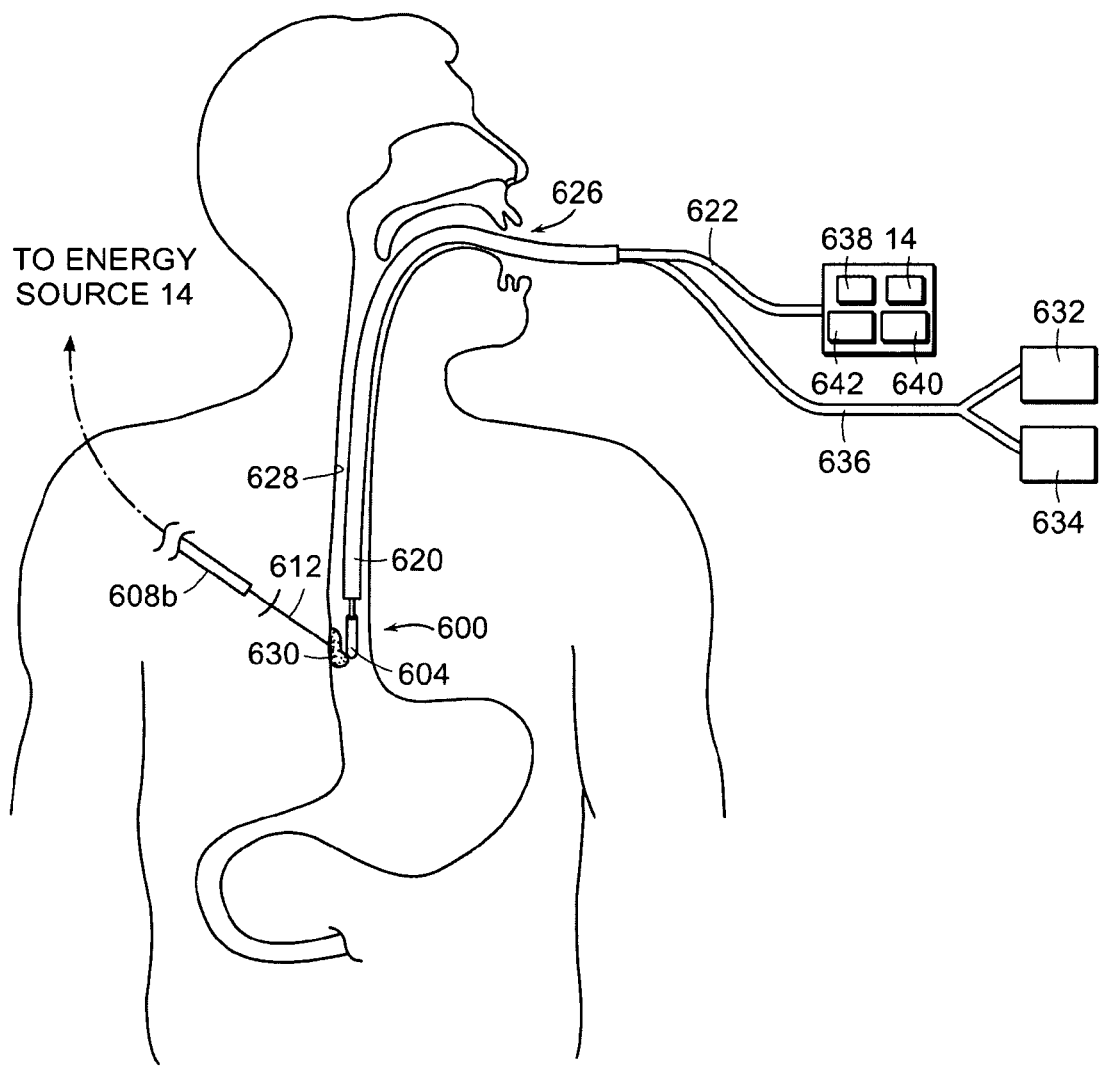

FIG. 15 illustrates one embodiment of the electrical ablation device shown in FIG. 13A inserted through the mouth and esophagus to ablate cancerous tissue in the esophagus using electrical pulses.

Figure 16:
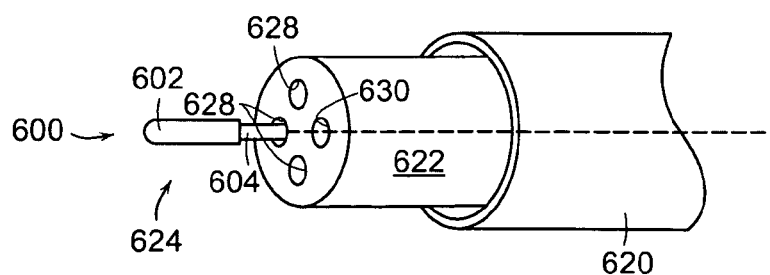

FIG. 16 illustrates a distal portion of an endoscope used in conjunction with the electrical ablation device shown in FIG. 13A.

Figure 17:
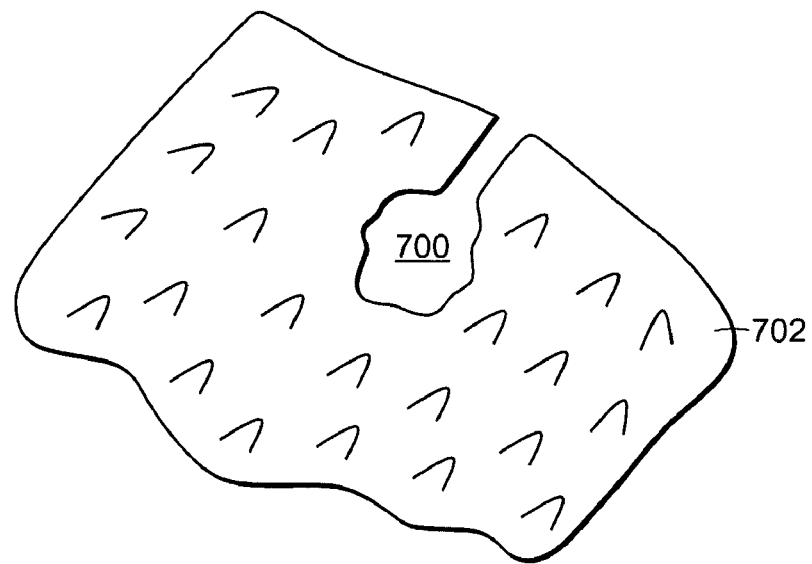

FIG. 17 illustrates a cross-sectional view of a breast showing a cavity that may be left after a lumpectomy to remove a tumor from the breast.

Figure 18:
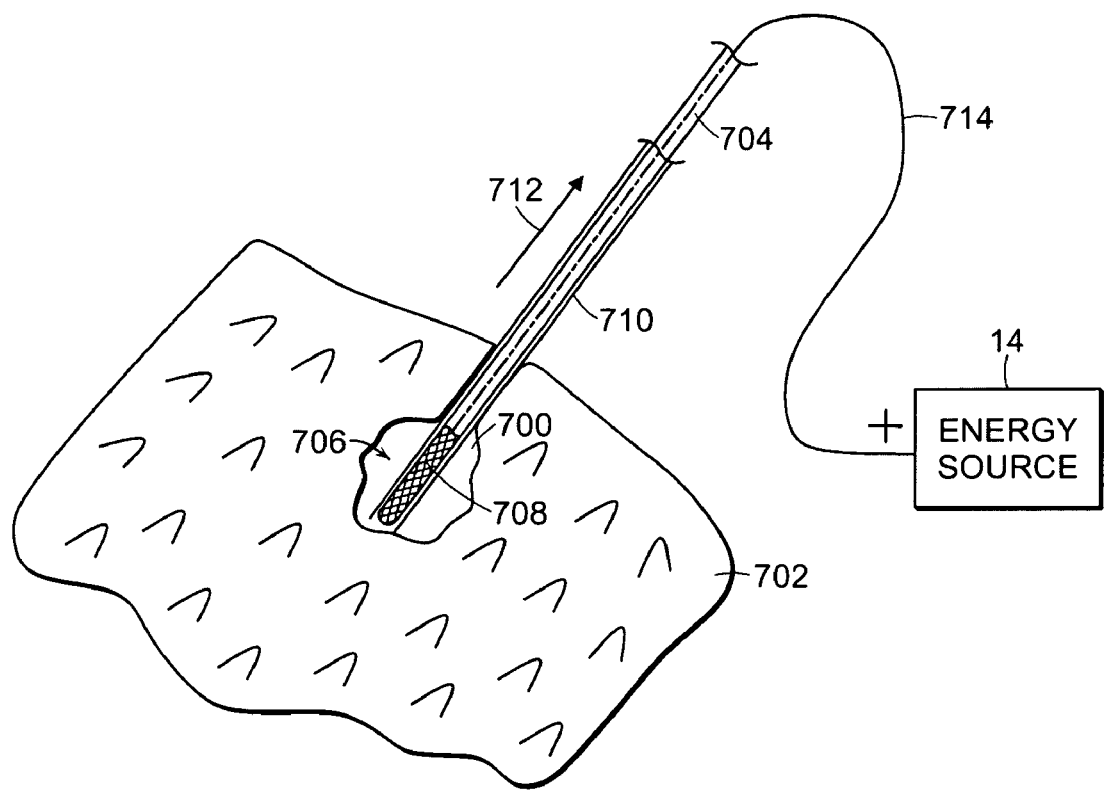

FIG. 18 illustrates one embodiment of a catheter inserted into the cavity left in the breast following a lumpectomy procedure as shown in FIG. 17.

Figure 19:
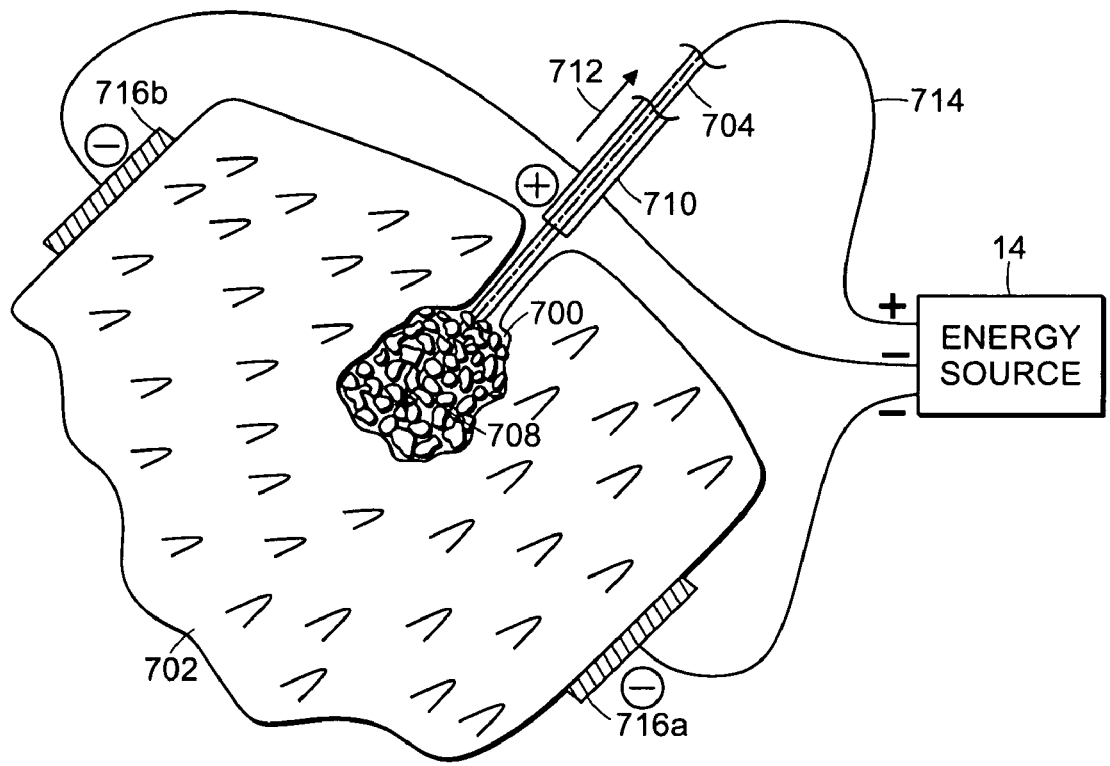

FIG. 19 illustrates an expanded sponge filling the cavity left in the breast following a lumpectomy as shown in FIG. 17.

Figure 20:
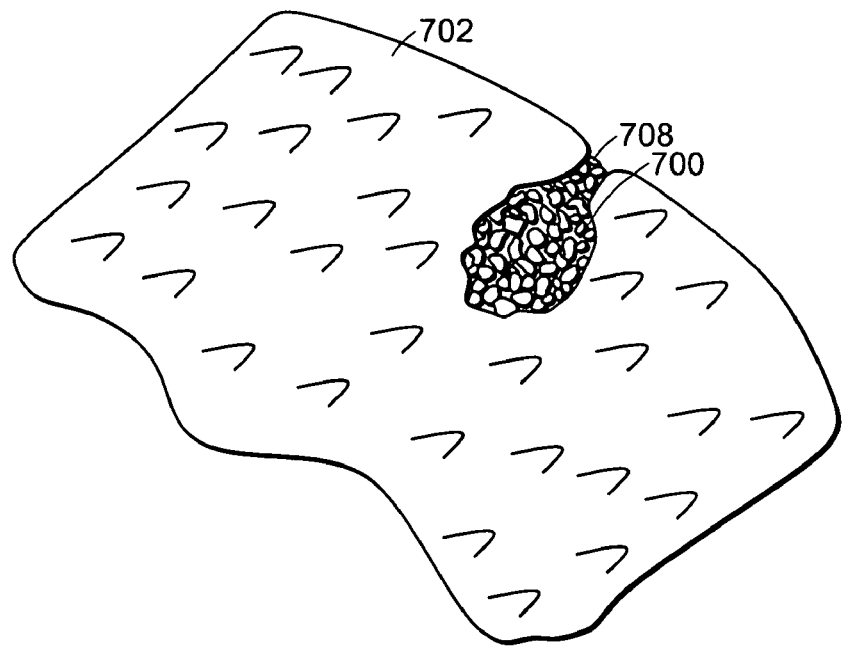

FIG. 20 illustrates the expanded sponge intact to fill the cavity left in the breast as shown in FIG. 17 following irreversible electroporation ablation therapy.

Figure 21:
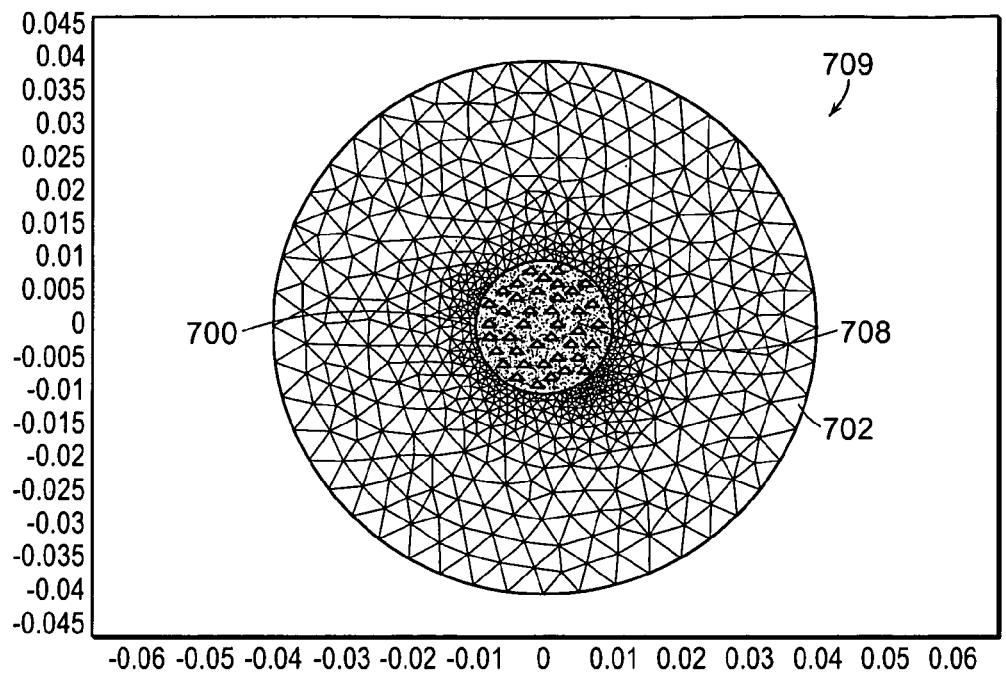

FIG. 21 illustrates a mesh of a finite element model of a sponge inserted in the cavity left in the breast as shown in FIG. 17.

Figure 22:
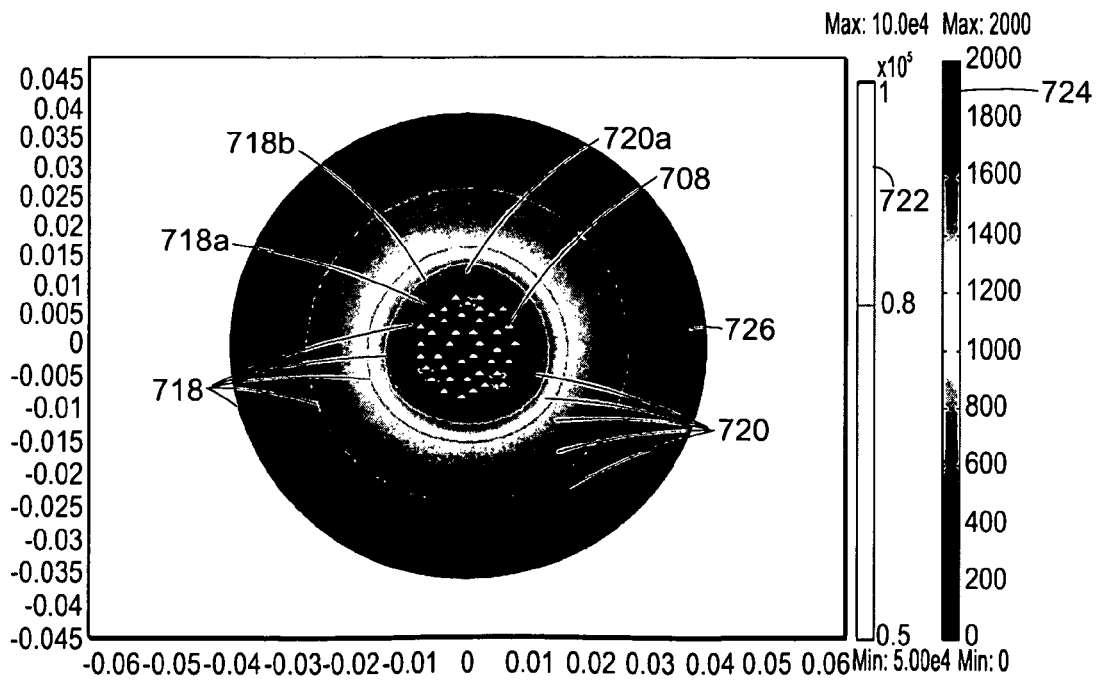

FIG. 22 is a graphical representation of electric potential and electrical field strength sufficient to induce irreversible electroporation when applied to the sponge located within the breast cavity as shown in FIG. 17.

Figure 23:
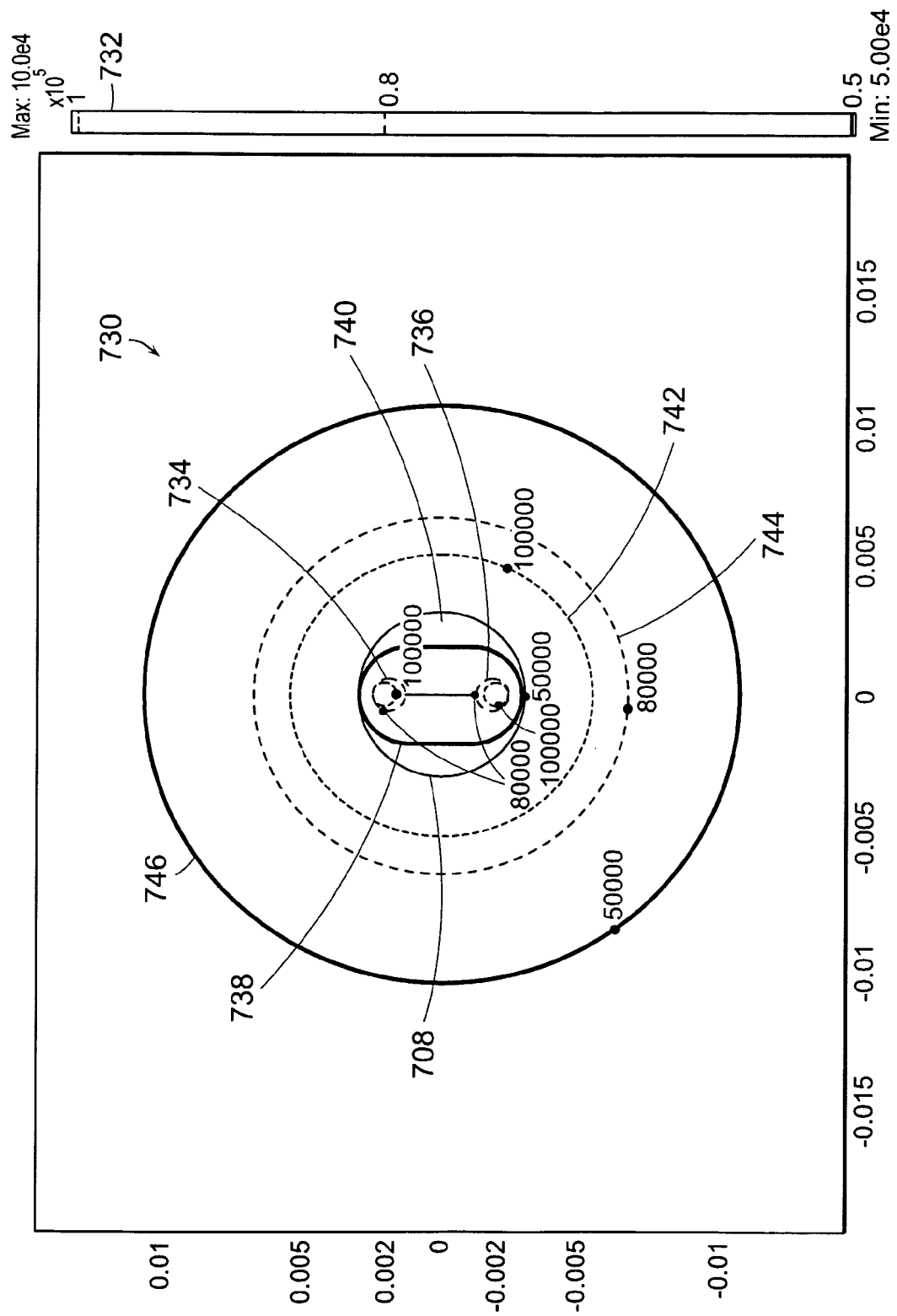

FIG. 23 is a graphical representation of electric field strength contours in volts per meter (V/m) developed when electrodes are energized by an energy source.

DESCRIPTION

Various embodiments are directed to apparatuses, systems, and methods for the electrical ablation treatment of undesirable tissue such as diseased tissue, cancer, malignant and benign tumors, masses, lesions, and other abnormal tissue growths without causing any detrimental thermal effects to surrounding healthy tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without the specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Various embodiments of apparatuses, systems, and methods for the electrical ablation treatment of undesirable tissue such as diseased tissue, cancer, malignant and benign tumors, masses, lesions, and other abnormal tissue growths, are described throughout the specification and illustrated in the accompanying drawings. The electrical ablation devices in accordance with the described embodiments may comprise one or more electrodes configured to be positioned into or proximal to undesirable tissue in a tissue treatment region (e.g., target site, worksite) where there is evidence of abnormal tissue growth, for example. In general, the electrodes comprise an electrically conductive portion (e.g., medical grade stainless steel) and are configured to electrically couple to an energy source. Once the electrodes are positioned into or proximal to the undesirable tissue, an energizing potential is applied to the electrodes to create an electric field to which the undesirable tissue is exposed. The energizing potential (and the resulting electric field) may be characterized by multiple parameters such as frequency, amplitude, pulse width (duration of a pulse or pulse length), and/or polarity. Depending on the diagnostic or therapeutic treatment to be rendered, a particular electrode may be configured either as an anode (+) or a cathode (−) or may comprise a plurality of electrodes with at least one configured as an anode and at least one other configured as a cathode. Regardless of the initial polar configuration, the polarity of the electrodes may be reversed by reversing the polarity of the output of the energy source.

In various embodiments, a suitable energy source may comprise an electrical waveform generator, which may be configured to create an electric field that is suitable to create irreversible electroporation in undesirable tissue at various electric filed amplitudes and durations. The energy source may be configured to deliver irreversible electroporation pulses in the form of direct-current (DC) and/or alternating-current (AC) voltage potentials (e.g., time-varying voltage potentials) to the electrodes. The irreversible electroporation pulses may be characterized by various parameters such as frequency, amplitude, pulse length, and/or polarity. The undesirable tissue may be ablated by exposure to the electric potential difference across the electrodes.

In one embodiment, the energy source may comprise a wireless transmitter to deliver energy to the electrodes using wireless energy transfer techniques via one or more remotely positioned antennas. Those skilled in the art will appreciate that wireless energy transfer or wireless power transmission is the process of transmitting electrical energy from an energy source to an electrical load without interconnecting wires. An electrical transformer is the simplest instance of wireless energy transfer. The primary and secondary circuits of a transformer are not directly connected and the transfer of energy takes place by electromagnetic coupling through a process known as mutual induction. Power also may be transferred wirelessly using RF energy. Wireless power transfer technology using RF energy is produced by Powercast, Inc. and can achieve an output of 6 volts for a little over one meter. Other low-power wireless power technology has been proposed such as described in U.S. Pat. No. 6,967,462.

The apparatuses, systems, and methods in accordance with the described embodiments may be configured for minimally invasive ablation treatment of undesirable tissue through the use of irreversible electroporation to be able to ablate undesirable tissue in a controlled and focused manner without inducing thermally damaging effects to the surrounding healthy tissue. The apparatuses, systems, and methods in accordance with the described embodiments may be configured to ablate undesirable tissue through the use of electroporation or electropermeabilization. More specifically, the apparatuses, systems, and methods in accordance with the described embodiments may be configured to ablate undesirable tissue through the use of irreversible electroporation. Electroporation increases the permeabilization of a cell membrane by exposing the cell to electric pulses. The external electric field (electric potential/per unit length) to which the cell membrane is exposed to significantly increases the electrical conductivity and permeability of the plasma in the cell membrane. The primary parameter affecting the transmembrane potential is the potential difference across the cell membrane. Irreversible electroporation is the application of an electric field of a specific magnitude and duration to a cell membrane such that the permeabilization of the cell membrane cannot be reversed, leading to cell death without inducing a significant amount of heat in the cell membrane. The destabilizing potential forms pores in the cell membrane when the potential across the cell membrane exceeds its dielectric strength causing the cell to die under a process known as apoptosis and/or necrosis. The application of irreversible electroporation pulses to cells is an effective way for ablating large volumes of undesirable tissue without deleterious thermal effects to the surrounding healthy tissue associated with thermal-inducing ablation treatments. This is because irreversible electroporation destroys cells without heat and thus does not destroy the cellular support structure or regional vasculature. A destabilizing irreversible electroporation pulse, suitable to cause cell death without inducing a significant amount of thermal damage to the surrounding healthy tissue, may have amplitude in the range of about several hundred to about several thousand volts and is generally applied across biological membranes over a distance of about several millimeters, for example, for a relatively long duration. Thus, the undesirable tissue may be ablated in-vivo through the delivery of destabilizing electric fields by quickly creating cell necrosis.

The apparatuses, systems, and methods for electrical ablation therapy in accordance with the described embodiments may be adapted for use in minimally invasive surgical procedures to access the tissue treatment region in various anatomic locations such as the brain, lungs, breast, liver, gall bladder, pancreas, prostate gland, and various internal body lumen defined by the esophagus, stomach, intestine, colon, arteries, veins, anus, vagina, cervix, fallopian tubes, and the peritoneal cavity, for example, without limitation. Minimally invasive electrical ablation devices may be introduced to the tissue treatment region using a trocar inserted though a small opening formed in the patient's body or through a natural body orifice such as the mouth, anus, or vagina using translumenal access techniques known as Natural Orifice Translumenal Endoscopic Surgery (NOTES)™. Once the electrical ablation devices (e.g., electrodes) are located into or proximal to the undesirable tissue in the treatment region, electric field potentials can be applied to the undesirable tissue by the energy source. The electrical ablation devices comprise portions that may be inserted into the tissue treatment region percutaneously (e.g., where access to inner organs or other tissue is done via needle-puncture of the skin). Other portions of the electrical ablation devices may be introduced into the tissue treatment region endoscopically (e.g., laparoscopically and/or thoracoscopically) through trocars or working channels of the endoscope, through small incisions, or transcutaneously (e.g., where electric pulses are delivered to the tissue treatment region through the skin).

FIG. 1 illustrates one embodiment of an electrical ablation system 10. The electrical ablation system 10 may be employed to ablate undesirable tissue such as diseased tissues, cancers, tumors, masses, lesions, abnormal tissue growths inside a patient using electrical energy. The electrical ablation system 10 may be used in conjunction with endoscopic, laparoscopic, thoracoscopic, open surgical procedures via small incisions or keyholes, percutaneous techniques, transcutaneous techniques, and/or external non-invasive techniques, or any combinations thereof without limitation. The electrical ablation system 10 may be configured to be positioned within a natural body orifice of the patient such as the mouth, anus, or vagina and advanced through internal body lumen or cavities such as the esophagus, colon, cervix, urethra, for example, to reach the tissue treatment region. The electrical ablation system 10 also may be configured to be positioned and passed through a small incision or keyhole formed through the skin or abdominal wall of the patient to reach the tissue treatment region using a trocar. The tissue treatment region may be located in the brain, lungs, breast, liver, gall bladder, pancreas, prostate gland, various internal body lumen defined by the esophagus, stomach, intestine, colon, arteries, veins, anus, vagina, cervix, fallopian tubes, and the peritoneal cavity, for example, without limitation. The electrical ablation system 10 can be configured to treat a number of lesions and ostepathologies comprising metastatic lesions, tumors, fractures, infected sites, inflamed sites. Once positioned into or proximate the tissue treatment region, the electrical ablation system 10 can be actuated (e.g., energized) to ablate the undesirable tissue. In one embodiment, the electrical ablation system 10 may be configured to treat diseased tissue in the gastrointestinal (GI) tract, esophagus, lung, or stomach that may be accessed orally. In another embodiment, the electrical ablation system 10 may be adapted to treat undesirable tissue in the liver or other organs that may be accessible using translumenal access techniques such as, without limitation, NOTES™ techniques, where the electrical ablation devices may be initially introduced through a natural orifice such as the mouth, anus, or vagina and then advanced to the tissue treatment site by puncturing the walls of internal body lumen such as the stomach, intestines, colon, cervix. In various embodiments, the electrical ablation system 10 may be adapted to treat undesirable tissue in the brain, liver, breast, gall bladder, pancreas, or prostate gland, using one or more electrodes positioned percutaneously, transcutaneously, translumenally, minimally invasively, and/or through open surgical techniques, or any combination thereof.

In one embodiment, the electrical ablation system 10 may be employed in conjunction with a flexible endoscope 12, as well as a rigid endoscope, laparoscope, or thoracoscope, such as the GIF-100 model available from Olympus Corporation.

In one embodiment, the endoscope 12 may be introduced to the tissue treatment region trans-anally through the colon, trans-orally through the esophagus and stomach, trans-vaginally through the cervix, transcutaneously, or via an external incision or keyhole formed in the abdomen in conjunction with a trocar. The electrical ablation system 10 may be inserted and guided into or proximate the tissue treatment region using the endoscope 12.

In the embodiment illustrated in FIG. 1, the endoscope 12 comprises an endoscope handle 34 and an elongate relatively flexible shaft 32. The distal end of the flexible shaft 32 may comprise a light source and a viewing port. Optionally, the flexible shaft 32 may define one or more working channels for receiving various instruments, such as electrical ablation devices, for example, therethrough. Images within the field of view of the viewing port are received by an optical device, such as a camera comprising a charge coupled device (CCD) usually located within the endoscope 12, and are transmitted to a display monitor (not shown) outside the patient.

In one embodiment, the electrical ablation system 10 may comprise an electrical ablation device 20, a plurality of electrical conductors 18, a handpiece 16 comprising an activation switch 62, and an energy source 14, such as an electrical waveform generator, electrically coupled to the activation switch 62 and the electrical ablation device 20. The electrical ablation device 20 comprises a relatively flexible member or shaft 22 that may be introduced to the tissue treatment region using a variety of known techniques such as an open incision and a trocar, through one of more of the working channels of the endoscope 12, percutaneously, or transcutaneously.

In one embodiment, one or more electrodes (e.g., needle electrodes, balloon electrodes), such as first and second electrodes 24a,b, extend out from the distal end of the electrical ablation device 20. In one embodiment, the first electrode 24a may be configured as the positive electrode and the second electrode 24b may be configured as the negative electrode. The first electrode 24a is electrically connected to a first electrical conductor 18a, or similar electrically conductive lead or wire, which is coupled to the positive terminal of the energy source 14 through the activation switch 62. The second electrode 24b is electrically connected to a second electrical conductor 18b, or similar electrically conductive lead or wire, which is coupled to the negative terminal of the energy source 14 through the activation switch 62. The electrical conductors 18a,b are electrically insulated from each other and surrounding structures, except for the electrical connections to the respective electrodes 24a,b. In various embodiments, the electrical ablation device 20 may be configured to be introduced into or proximate the tissue treatment region using the endoscope 12 (laparoscope or thoracoscope), open surgical procedures, or external and non-invasive medical procedures. The electrodes 24a,b may be referred to herein as endoscopic or laparoscopic electrodes, although variations thereof may be inserted transcutaneously or percutaneously. As previously discussed, either one or both electrodes 24a,b may be adapted and configured to slideably move in and out of a cannula, lumen, or channel defined within the flexible shaft 22.

Once the electrodes 24a,b are positioned at the desired location into or proximate the tissue treatment region, the electrodes 24a,b may be connected to or disconnected from the energy source 14 by actuating or de-actuating the switch 62 on the handpiece 16. The switch 62 may be operated manually or may be mounted on a foot switch (not shown), for example. The electrodes 24a,b deliver electric field pulses to the undesirable tissue. The electric field pulses may be characterized based on various parameters such as pulse shape, amplitude, frequency, and duration. The electric field pulses may be sufficient to induce irreversible electroporation in the undesirable tissue. The induced potential depends on a variety of conditions such as tissue type, cell size, and electrical pulse parameters. The primary electrical pulse parameter affecting the transmembrane potential for a specific tissue type is the amplitude of the electric field and pulse length that the tissue is exposed to.

In one embodiment, a protective sleeve or sheath 26 may be slidably disposed over the flexible shaft 22 and within a handle 28. In another embodiment, the sheath 26 may be slidably disposed within the flexible shaft 22 and the handle 28, without limitation. The sheath 26 is slideable and may be located over the electrodes 24a,b to protect the trocar and prevent accidental piercing when the electrical ablation device 20 is advanced therethrough. Either one or both of the electrodes 24a,b of the electrical ablation device 20 may be adapted and configured to slideably move in and out of a cannula, lumen, or channel formed within the flexible shaft 22. The second electrode 24b may be fixed in place. The second electrode 24b may provide a pivot about which the first electrode 24a can be moved in an arc to other points in the tissue treatment region to treat larger portions of the diseased tissue that cannot be treated by fixing the electrodes 24a,b in one location. In one embodiment, either one or both of the electrodes 24a,b may be adapted and configured to slideably move in and out of a working channel formed within a flexible shaft 32 of the flexible endoscope 12 or may be located independently of the flexible endoscope 12. Various features of the first and second electrodes 24a,b are described in more detail in FIGS. 2A-D.

In one embodiment, the first and second electrical conductors 18a,b may be provided through the handle 28. In the illustrated embodiment, the first electrode 24a can be slideably moved in and out of the distal end of the flexible shaft 22 using a slide member 30 to retract and/or advance the first electrode 24a. In various embodiments either or both electrodes 24a,b may be coupled to the slide member 30, or additional slide members, to advance and retract the electrodes 24a,b, e.g., position the electrodes 24a,b. In the illustrated embodiment, the first electrical conductor 18a coupled to the first electrode 24a is coupled to the slide member 30. In this manner, the first electrode 24a, which is slidably movable within the cannula, lumen, or channel defined by the flexible shaft 22, can advanced and retracted with the slide member 30.

In various other embodiments, transducers or sensors 29 may be located in the handle 28 of the electrical ablation device 20 to sense the force with which the electrodes 24a,b penetrate the tissue in the tissue treatment zone. This feedback information may be useful to determine whether either one or both of the electrodes 24a,b have been properly inserted in the tissue treatment region. As is particularly well known, cancerous tumor tissue tends to be denser than healthy tissue and thus greater force is required to insert the electrodes 24a,b therein. The transducers or sensors 29 can provide feedback to the operator, surgeon, or clinician to physically sense when the electrodes 24a,b are placed within the cancerous tumor. The feedback information provided by the transducers or sensors 29 may be processed and displayed by circuits located either internally or externally to the energy source 14. The sensor 29 readings may be employed to determine whether the electrodes 24a,b have been properly located within the cancerous tumor thereby assuring that a suitable margin of error has been achieved in locating the electrodes 24a,b.

In one embodiment, the input to the energy source 14 may be connected to a commercial power supply by way of a plug (not shown). The output of the energy source 14 is coupled to the electrodes 24a,b, which may be energized using the activation switch 62 on the handpiece 16, or in one embodiment, an activation switch mounted on a foot activated pedal (not shown). The energy source 14 may be configured to produce electrical energy suitable for electrical ablation, as described in more detail below.

In one embodiment, the electrodes 24a,b are adapted and configured to electrically couple to the energy source 14 (e.g., generator, waveform generator). Once electrical energy is coupled to the electrodes 24a,b, an electric field is formed at a distal end of the electrodes 24a,b. The energy source 14 may be configured to generate electric pulses at a predetermined frequency, amplitude, pulse length, and/or polarity that are suitable to induce irreversible electroporation to ablate substantial volumes of undesirable tissue in the treatment region. For example, the energy source 14 may be configured to deliver DC electric pulses having a predetermined frequency, amplitude, pulse length, and/or polarity suitable to induce irreversible electroporation to ablate substantial volumes of undesirable tissue in the treatment region. The DC pulses may be positive or negative relative to a particular reference polarity. The polarity of the DC pulses may be reversed or inverted from positive-to-negative or negative-to-positive a predetermined number of times to induce irreversible electroporation to ablate substantial volumes of undesirable tissue in the treatment region.

In one embodiment, a timing circuit may be coupled to the output of the energy source 14 to generate electric pulses. The timing circuit may comprise one or more suitable switching elements to produce the electric pulses. For example, the energy source 14 may produce a series of n electric pulses (where n is any positive integer) of sufficient amplitude and duration to induce irreversible electroporation suitable for tissue ablation when the n electric pulses are applied to the electrodes 24a,b. In one embodiment, the electric pulses may have a fixed or variable pulse length, amplitude, and/or frequency.

The electrical ablation device 20 may be operated either in bipolar or monopolar mode. In bipolar mode, the first electrode 24a is electrically connected to a first polarity and the second electrode 24b is electrically connected to the opposite polarity. For example, in monopolar mode, the first electrode 24a is coupled to a prescribed voltage and the second electrode 24b is set to ground. In the illustrated embodiment, the energy source 14 may be configured to operate in either the bipolar or monopolar modes with the electrical ablation system 10. In bipolar mode, the first electrode 24a is electrically connected to a prescribed voltage of one polarity and the second electrode 24b is electrically connected to a prescribed voltage of the opposite polarity. When more than two electrodes are used, the polarity of the electrodes may be alternated so that any two adjacent electrodes may have either the same or opposite polarities, for example.

In monopolar mode, it is not necessary that the patient be grounded with a grounding pad. Since a monopolar energy source 14 is typically constructed to operate upon sensing a ground pad connection to the patient, the negative electrode of the energy source 14 may be coupled to an impedance simulation circuit. In this manner, the impedance circuit simulates a connection to the ground pad and thus is able to activate the energy source 14. It will be appreciated that in monopolar mode, the impedance circuit can be electrically connected in series with either one of the electrodes 24a,b that would otherwise be attached to a grounding pad.

In one embodiment, the energy source 14 may be configured to produce RF waveforms at predetermined frequencies, amplitudes, pulse widths or durations, and/or polarities suitable for electrical ablation of cells in the tissue treatment region. One example of a suitable RF energy source is a commercially available conventional, bipolar/monopolar electrosurgical RF generator such as Model Number ICC 350, available from Erbe, GmbH.

In one embodiment, the energy source 14 may be configured to produce destabilizing electrical potentials (e.g., fields) suitable to induce irreversible electroporation. The destabilizing electrical potentials may be in the form of bipolar/monopolar DC electric pulses suitable for inducing irreversible electroporation to ablate tissue undesirable tissue with the electrical ablation device 20. A commercially available energy source suitable for generating irreversible electroporation electric filed pulses in bipolar or monopolar mode is a pulsed DC generator such as Model Number ECM 830, available from BTX Molecular Delivery Systems Boston, Mass. In bipolar mode, the first electrode 24a may be electrically coupled to a first polarity and the second electrode 24b may be electrically coupled to a second (e.g., opposite) polarity of the energy source 14. Bipolar/monopolar DC electric pulses may be produced at a variety of frequencies, amplitudes, pulse lengths, and/or polarities. Unlike RF ablation systems, however, which require high power and energy levels delivered into the tissue to heat and thermally destroy the tissue, irreversible electroporation requires very little energy input into the tissue to kill the undesirable tissue without the detrimental thermal effects because with irreversible electroporation the cells are destroyed by electric field potentials rather than heat.

In one embodiment, the energy source 14 may be coupled to the first and second electrodes 24a,b by either a wired or a wireless connection. In a wired connection, the energy source 14 is coupled to the electrodes 24a,b by way of the electrical conductors 18a,b, as shown. In a wireless connection, the electrical conductors 18a,b may be replaced with a first antenna (not shown) coupled the energy source 14 and a second antenna (not shown) coupled to the electrodes 24a,b, wherein the second antenna is remotely located from the first antenna. In one embodiment, the energy source may comprise a wireless transmitter to deliver energy to the electrodes using wireless energy transfer techniques via one or more remotely positioned antennas. As previously discussed, wireless energy transfer or wireless power transmission is the process of transmitting electrical energy from the energy source 14 to an electrical load, e.g., the abnormal cells in the tissue treatment region, without using the interconnecting electrical conductors 18a,b. An electrical transformer is the simplest instance of wireless energy transfer. The primary and secondary circuits of a transformer are not directly connected. The transfer of energy takes place by electromagnetic coupling through a process known as mutual induction. Wireless power transfer technology using RF energy is produced by Powercast, Inc. The Powercast system can achieve a maximum output of 6 volts for a little over one meter. Other low-power wireless power technology has been proposed such as described in U.S. Pat. No. 6,967,462.

In one embodiment, the energy source 14 may be configured to produce DC electric pulses at frequencies in the range of about 1 Hz to about 10000 Hz, amplitudes in the range of about ±100 to about ±3000 VDC, and pulse lengths (e.g., pulse width, pulse duration) in the range of about 1 µs to about 100 ms. The polarity of the electric potentials coupled to the electrodes 24a,b may be reversed during the electrical ablation therapy. For example, initially, the DC electric pulses may have a positive polarity and an amplitude in the range of about +100 to about +3000 VDC. Subsequently, the polarity of the DC electric pulses may be reversed such that the amplitude is in the range of about −100 to about −3000 VDC. In one embodiment, the undesirable cells in the tissue treatment region may be electrically ablated with DC pulses suitable to induce irreversible electroporation at frequencies of about 10 Hz to about 100 Hz, amplitudes in the range of about +700 to about +1500 VDC, and pulse lengths of about 10 µs to about 50 µs. In another embodiment, the abnormal cells in the tissue treatment region may be electrically ablated with an electrical waveform having an amplitude of about +500 VDC and pulse duration of about 20 ms delivered at a pulse period T or repetition rate, frequency f=1/T, of about 10 Hz. It has been determined that an electric field strength of 1,000V/cm is suitable for destroying living tissue by inducing irreversible electroporation.

Figure 2A:
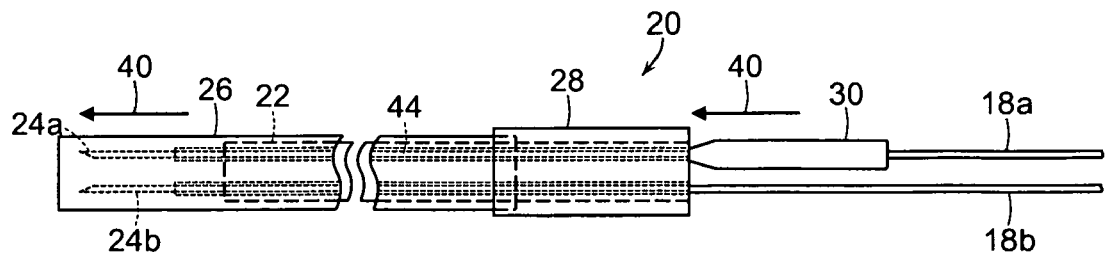
FIG. 2E illustrates one embodiment of the electrical ablation device comprising multiple needle electrodes.
Figure 2B:
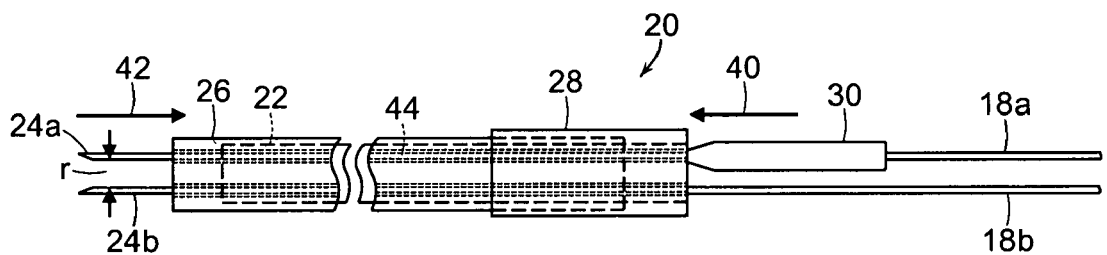
Figure 2C:
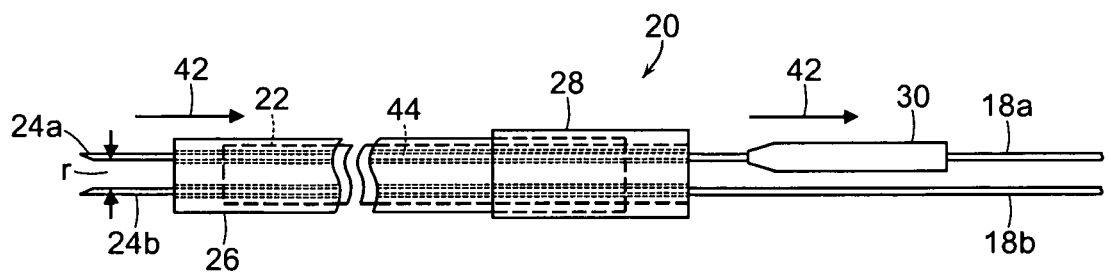
Figure 2D:
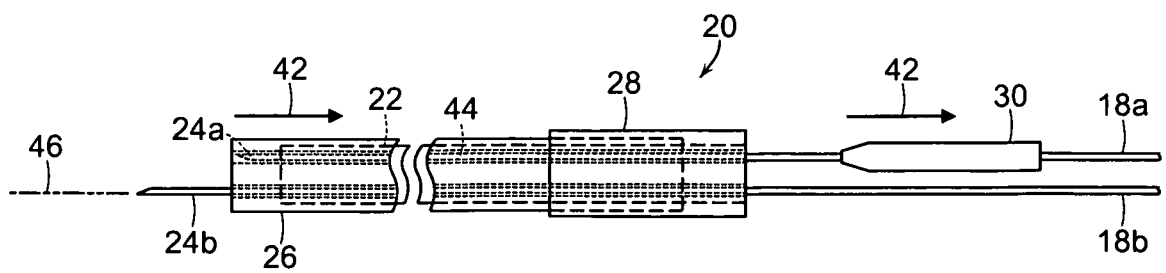
Figure 3:
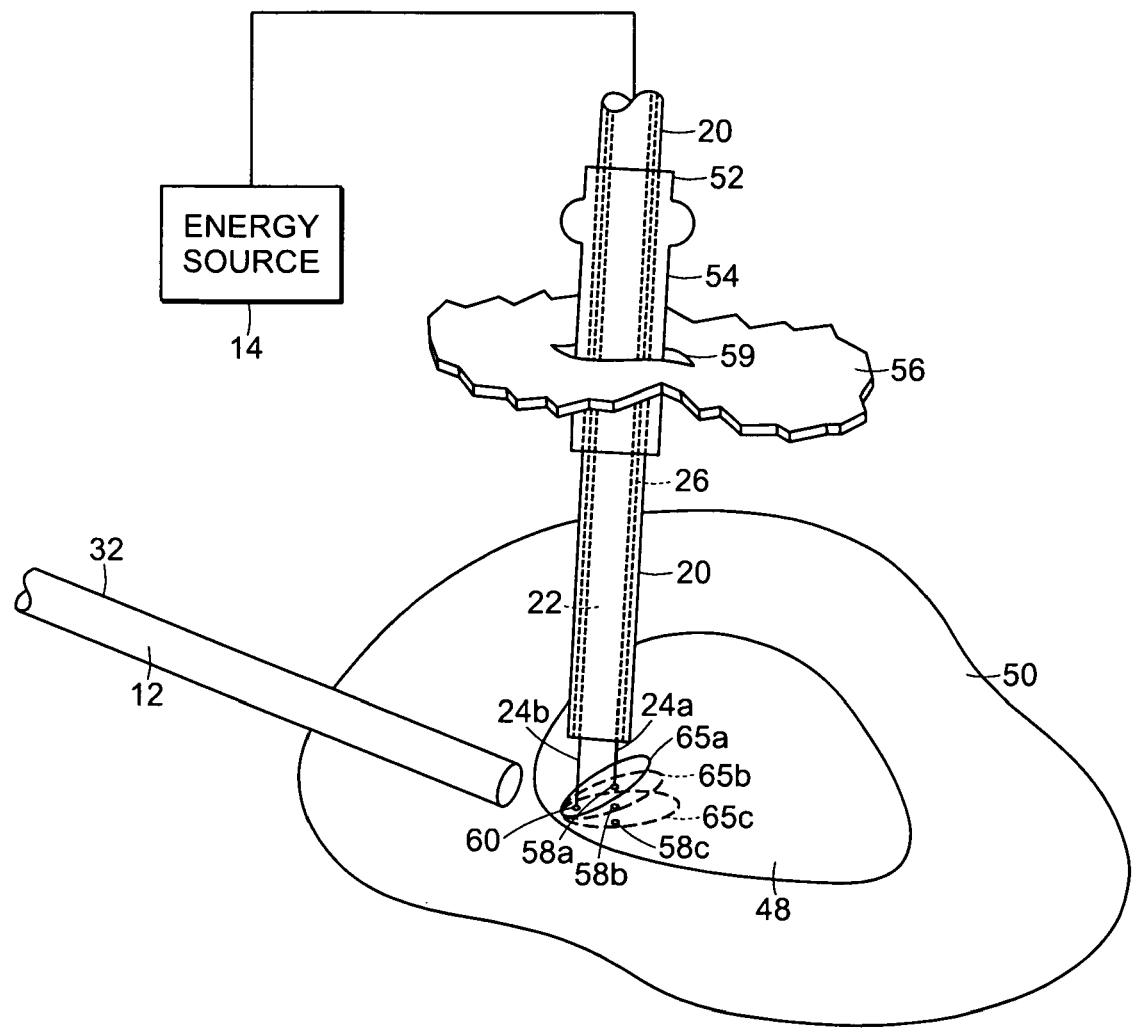
FIG. 3 illustrates one embodiment of the electrical ablation system shown in FIGS. 1 and 2A-D in use to treat undesirable tissue located on the surface of the liver.

FIGS. 2A-D illustrate one embodiment of the electrical ablation device 20 in various phases of deployment. In the embodiment illustrated in FIGS. 2A-D, the sheath 26 is disposed over the flexible shaft 22, however, those skilled in the art will appreciate that the sheath 26 may be disposed within the flexible shaft 22. The electrical ablation device 20 may be used in conjunction with the electrical ablation system 10 shown in FIG. 1. It will be appreciated that other devices and electrode configurations may be employed without limitation. FIG. 2A illustrates an initial phase of deployment wherein the sheath 26 is extended in the direction indicated by arrow 40 to cover the electrodes 24a,b. The electrodes 24a,b may have dimensions of about 0.5 mm, about 1 mm, or about 1.5 mm in diameter. It will be appreciated that the dimensions of the electrodes 24a,b may be anywhere from about 0.5 mm to about 1.5 mm in diameter. The electrical ablation device 20 may be introduced into the tissue treatment region through a trocar, as illustrated in FIG. 3, for example. FIG. 2B illustrates another phase of deployment wherein the sheath 26 is retracted within the handle 28 in the direction indicated by arrow 42. In this phase of deployment, the first and second electrodes 24a,b extend through the distal end of the flexible shaft 22 and are ready to be inserted into or proximate the tissue treatment region. The first electrode 24a may be retracted in direction 42 through a lumen 44 formed in the flexible shaft 22 by holding the handle 28 and pulling on the slide member 30. FIG. 2C illustrates a transition phase wherein the first electrode 24a is the process of being retracted in direction 42 by pulling on the slide member 30 handle, for example, in the same direction. FIG. 2D illustrates another phase of deployment wherein the first electrode 24a is in a fully retracted position. In this phase of deployment the electrical ablation device 20 can be pivotally rotated about an axis 46 defined by the second electrode 24b. The electrodes 24a,b are spaced apart by a distance "r." The distance "r" between the electrodes 24a,b may be 5.0 mm, about 7.5 mm, or about 10 mm. It will be appreciated that the distance "r" between the electrodes 24a,b may be anywhere from about 5.0 mm to about 10.0 mm. Thus, the electrical ablation device 20 may be rotated in an arc about the pivot formed by the second electrode 24b, the first electrode 24a may be placed in a new location in the tissue treatment region within the radius "r." Retracting the first electrode 24a and pivoting about the second electrode 24b enables the surgeon or clinician to target and treat a larger tissue treatment region essentially comprising a circular region having a radius "r," which is the distance between the electrodes 24a,b. Thus, the electrodes 24a,b may be located in a plurality of positions in and around the tissue treatment region in order to treat much larger regions of tissue. Increasing the electrode 24a,b diameter and spacing the electrodes 24a,b further apart enables the generation of an electric field over a much larger tissue regions and thus the ablation of larger volumes of undesirable tissue. In this manner, the operator can treat a larger tissue treatment region comprising cancerous lesions, polyps, or tumors, for example.

Although the electrical ablation electrodes according to the described embodiments have been described in terms of the particular needle type electrodes 24a,b as shown and described in FIGS. 1 and 2A-D, those skilled in the art will appreciate that other configurations of electrical ablation electrodes may be employed for the ablation of undesirable tissue, without limitation. In one embodiment, the electrical ablation device 20 may comprise two or more fixed electrodes that are non-retractable. In another embodiment, the electrical ablation device 20 may comprise two or more retractable electrodes, one embodiment of which is described below with reference to FIG. 2E. In another embodiment, the electrical ablation device 20 may comprise at least one slidable electrode disposed within at least one working channel of the flexible shaft 32 of the endoscope 12. In another embodiment, the electrical ablation device 20 may comprise at least one electrode may be configured to be inserted into the tissue treatment region transcutaneously or percutaneously. Still in various other embodiments, the electrical ablation device 20 may comprise at least one electrode configured to be introduced to the tissue treatment region transcutaneously or percutaneously and at least one other electrode may be configured to be introduced to the tissue treatment region through at least one working channel of the flexible shaft 32 of the endoscope 12. The embodiments, however, are not limited in this context.

Figure 2E:
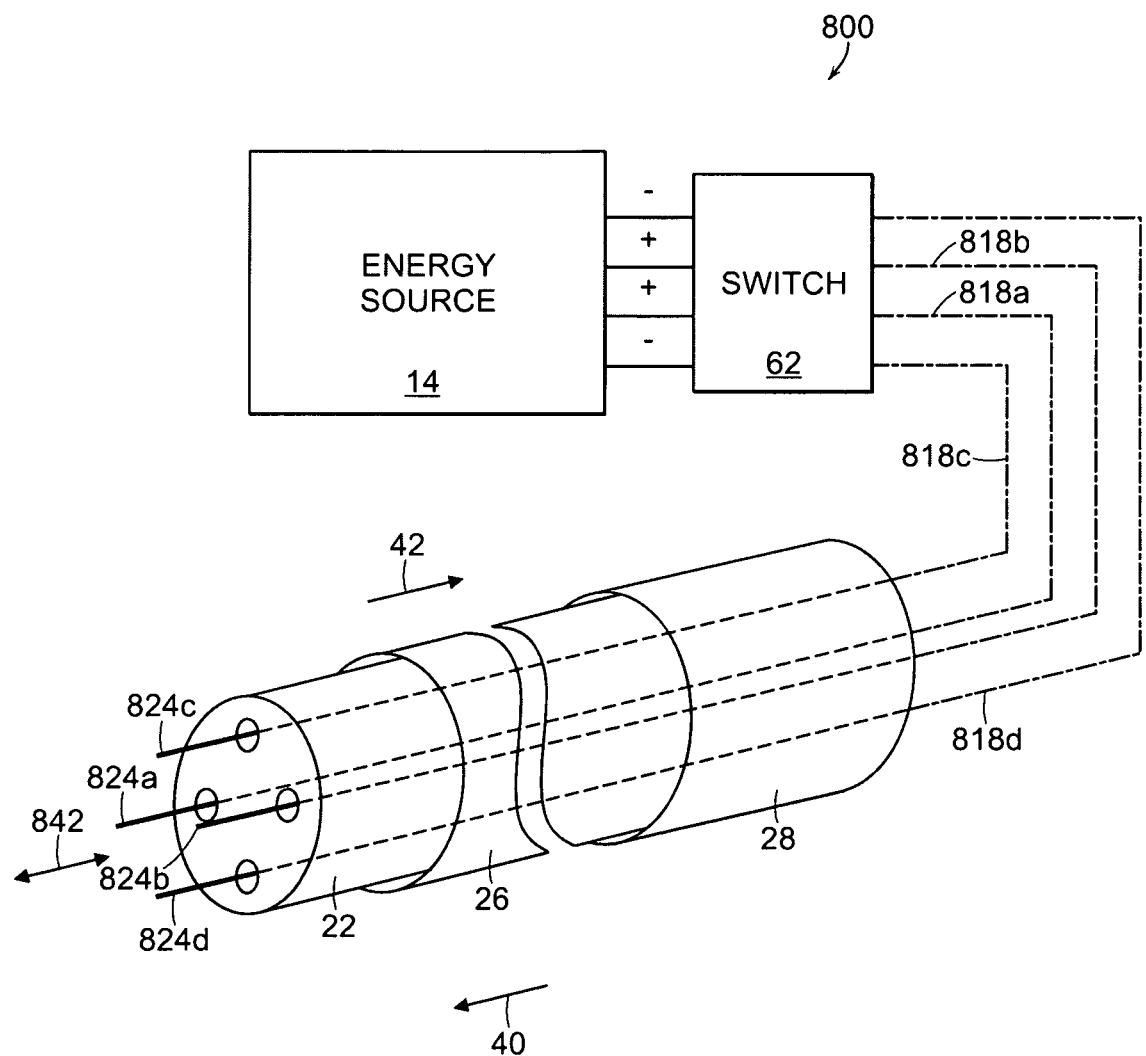

FIG. 2E illustrates one embodiment of an electrical ablation device 800 comprising multiple needle electrodes 824m, where m is any positive integer. In the illustrated embodiment, the electrical ablation device 800 comprises four electrodes 824a, 824b, 824c, 824d. It will be appreciated that in one embodiment, the electrical ablation device 800 also may comprise three needle electrodes 824a, 824b, 824c, without limitation. The electrical ablation device 800 may be used in conjunction with the electrical ablation system 10 shown in FIG. 1. It will be appreciated that other devices and electrode configurations may be employed without limitation. The electrodes 824a-m each may have dimensions of about 0.5 mm, about 1 mm, or about 1.5 mm in diameter. It will be appreciated that the dimensions of each of the electrodes 824a-m may be anywhere from about 0.5 mm to about 1.5 mm in diameter. The electrical ablation device 800 may be introduced into the tissue treatment region through a trocar, as subsequently described and illustrated with reference to FIG. 3, for example.

The electrical ablation device 800 comprises essentially the same components as the electrical ablation device 20 described with reference to FIGS. 2A-D. The electrical ablation device 800 comprises the relatively flexible member or shaft 22, the protective sheath 26, and one or more handles 28 to operate either the sheath 26, the electrodes 824a,b,c,d, or both. The electrodes 824a,b,c,d may be individually or simultaneously deployable and/or retractable in the direction indicated by arrow 842. The electrodes 824a,b,c,d extend out from the distal end of the electrical ablation device 800. In one embodiment, the first and second electrodes 824a, 824b may be configured as the positive electrode coupled to the anode of the energy source 14 via corresponding first and second electrical conductors 818a, 818b, and the third and fourth 824c, 824d may be configured as the negative electrode coupled to the cathode of the energy source 14 via corresponding third and fourth electrical conductors 818c, 818d, or similar electrically conductive leads or wires, through the activation switch 62. Once the electrodes 824a,b,c,d are positioned at the desired location into or proximate the tissue treatment region, the electrodes 824a,b,c,d may be connected/disconnected from the energy source 14 by actuating/de-actuating the switch 62.

As previously discussed with reference to FIGS. 2A-D, as shown in FIG. 2E in one embodiment, the protective sleeve or sheath 26 may be slidably disposed over the flexible shaft 22 and within the handle 28. In an initial phase of deployment, the sheath 26 is extended in direction 40 to cover the electrodes 824a,b,c,d to protect the trocar and prevent accidental piercing when the electrical ablation device 800 is advanced therethrough. Once the electrodes 824a,b,c,d are located into or proximate the tissue treatment region, the sheath 26 is retracted in direction 42 to expose the electrodes 824a,b,c,d. One or more of the electrodes 824a,b,c,d of the electrical ablation device 800 may be adapted and configured to slideably move in and out of a cannula, lumen, or channel formed within the flexible shaft 22. In one embodiment all of the electrodes 824a,b,c,d are configured to slideably move in and out channels formed within lumens formed within the flexible shaft 22, referred to for example as the lumen 44 in FIGS. 2A-D, to advance and retract the electrodes 824a,b,c,d as may be desired by the operator. Nevertheless, in other embodiments, it may be desired to fix all or certain ones of the one or more electrodes 824a,b,c,d in place.

The various embodiments of electrodes described in the present specification, e.g., the electrodes 24a,b, or 824a-m, may be configured for use with an electrical ablation device (not shown) comprising an elongated flexible shaft to house the needle electrodes 24a,b, or 824a-m, for example. The needle electrodes 24a,b, or 824a-m, are free to extend past a distal end of the electrical ablation device. The flexible shaft comprises multiple lumen formed therein to slidably receive the needle electrodes 24a,b, or 824a-m. A flexible sheath extends longitudinally from a handle portion to the distal end. The handle portion comprises multiple slide members received in respective slots defining respective walls. The slide members are coupled to the respective needle electrodes 24a,b, or 824a-m. The slide members are movable to advance and retract the electrode 24a,b, or 824a-m. The needle electrodes 24a,b, or 824a-m, may be independently movable by way of the respective slide members. The needle electrodes 24a,b, or 824a-m, may be deployed independently or simultaneously. An electrical ablation device (not shown) comprising an elongated flexible shaft to house multiple needle electrodes and a suitable handle is described with reference to FIGS. 4-10 in commonly owned U.S. patent application Ser. No. 11/897,676 titled "ELECTRICAL ABLATION SURGICAL INSTRUMENTS," filed Aug. 31, 2007, the entire disclosure of which is incorporated herein by reference in its entirety.

It will be appreciated that the electrical ablation devices 20, 800 described with referenced to FIGS. 2A-E, may be introduced inside a patient endoscopically (as shown in FIG. 15), transcutaneously, percutaneously, through an open incision, through a trocar (as shown in FIG. 3), through a natural orifice (as shown in FIG. 15), or any combination thereof. In one embodiment, the outside diameter of the electrical ablation devices 20, 800 may be sized to fit within a working channel of an endoscope and in other embodiments the outside diameter of the electrical ablation devices 20, 800 may be sized to fit within a hollow outer sleeve 620, or trocar, as shown in FIG. 15, for example. The hollow outer sleeve 620 or trocar is inserted into the upper gastrointestinal tract of a patient and may be sized to also receive a flexible endoscopic portion of an endoscope 622 (e.g., gastroscope), similar to the endoscope 12 described in FIG. 1.

FIG. 3 illustrates one embodiment of the electrical ablation system 10 shown in FIGS. 1 and 2A-D in use to treat undesirable tissue 48 located on the surface of the liver 50. The undesirable tissue 48 may be representative of a variety of diseased tissues, cancers, tumors, masses, lesions, abnormal tissue growths, for example. In use, the electrical ablation device 20 may be introduced into or proximate the tissue treatment region through a port 52 of a trocar 54. The trocar 54 is introduced into the patient via a small incision 59 formed in the skin 56. The endoscope 12 may be introduced into the patient trans-anally through the colon, trans-orally down the esophagus and through the stomach using translumenal techniques, or through a small incision or keyhole formed through the patient's abdominal wall (e.g., the peritoneal wall). The endoscope 12 may be employed to guide and locate the distal end of the electrical ablation device 20 into or proximate the undesirable tissue 48. Prior to introducing the flexible shaft 22 through the trocar 54, the sheath 26 is slid over the flexible shaft 22 in a direction toward the distal end thereof to cover the electrodes 24a,b (as shown in FIG. 2A) until the distal end of the electrical ablation device 20 reaches the undesirable tissue 48.

Once the electrical ablation device 20 has been suitably introduced into or proximate the undesirable tissue 48, the sheath 26 is retracted to expose the electrodes 24a,b (as shown in FIG. 2B) to treat the undesirable tissue 48. To ablate the undesirable tissue 48, the operator initially may locate the first electrode 24a at a first position 58a and the second electrode 24b at a second position 60 using endoscopic visualization and maintaining the undesirable tissue 48 within the field of view of the flexible endoscope 12. The first position 58a may be near a perimeter edge of the undesirable tissue 48. Once the electrodes 24a,b are located into or proximate the undesirable tissue 48, the electrodes 24a,b are energized with irreversible electroporation pulses to create a first necrotic zone 65a. For example, once the first and second electrodes 24a,b are located in the desired positions 60 and 58a, the undesirable tissue 48 may be exposed to an electric field generated by energizing the first and second electrodes 24a,b with the energy source 14. The electric field may have a magnitude, frequency, and pulse length suitable to induce irreversible electroporation in the undesirable tissue 48 within the first necrotic zone 65a. The size of the necrotic zone is substantially dependent on the size and separation of the electrodes 24a,b, as previously discussed. The treatment time is defined as the time that the electrodes 24a,b are activated or energized to generate the electric pulses suitable for inducing irreversible electroporation in the undesirable tissue 48.

This procedure may be repeated to destroy relatively larger portions of the undesirable tissue 48. The position 60 may be taken as a pivot point about which the first electrode 24a may be rotated in an arc of radius "r," the distance between the first and second electrodes 24a,b. Prior to rotating about the second electrode 24b, the first electrode 24a is retracted by pulling on the slide member 30 (FIGS. 1 and 2A-D) in a direction toward the proximal end and rotating the electrical ablation device 20 about the pivot point formed at position 60 by the second electrode 24b. Once the first electrode 24a is rotated to a second position 58b, it is advanced to engage the undesirable tissue 48 at point 58b by pushing on the slide member 30 in a direction towards the distal end. A second necrotic zone 65b is formed upon energizing the first and second electrodes 24a,b. A third necrotic zone 65c is formed by retracting the first electrode 24a, pivoting about pivot point 60 and rotating the first electrode 24a to a new location, advancing the first electrode 24a into the undesirable tissue 48 and energizing the first and second electrodes 24a,b. This process may be repeated as often as necessary to create any number of necrotic zones 65p, where p is any positive integer, within multiple circular areas of radius "r," for example, that is suitable to ablate the entire undesirable tissue 48 region. At anytime, the surgeon or clinician can reposition the first and second electrodes 24a,b and begin the process anew. In other embodiments, the electrical ablation device 800 comprising multiple needle electrodes 824a-m described with reference to FIG. 2E may be employed to treat the undesirable tissue 48. Those skilled in the art will appreciate that similar techniques may be employed to ablate any other undesirable tissues that may be accessible trans-anally through the colon, and/or orally through the esophagus and the stomach using translumenal access techniques. Therefore, the embodiments are not limited in this context.

Figure 4:
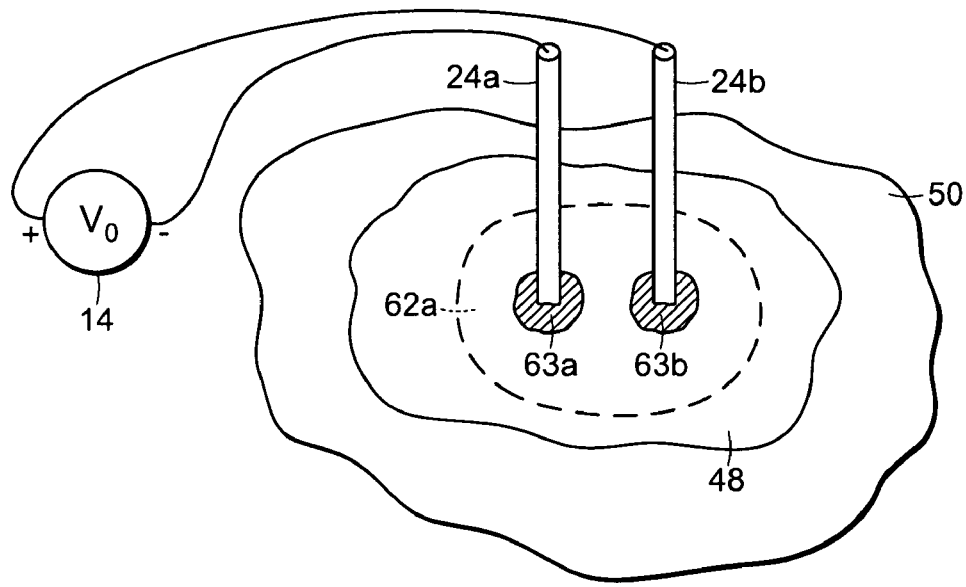
FIG. 4 illustrates a detailed view of one embodiment of the electrical ablation system shown in FIG. 3 in use to treat undesirable tissue located on the surface of the liver.

FIG. 4 illustrates a detailed view of one embodiment of the electrical ablation system 10 shown in FIG. 3 in use to treat undesirable tissue 48 located on the surface of the liver 50. The first and second electrodes 24a,b are embedded into or proximate the undesirable tissue 48 on the liver 50. The first and second electrodes 24a,b are energized to deliver one or more electrical pulses of amplitude and length sufficient to induce irreversible electroporation in the undesirable tissue 48 and create the first necrotic zone 65a. Additional electric pulses may be applied to the tissue immediately surrounding the respective electrodes 24a,b to form second, thermal, necrotic zones 63a,b near the electrode-tissue-interface. The duration of an irreversible electroporation energy pulse determines whether the temperature of the tissue 63a,b immediately surrounding the respective electrodes 24a,b raises to a level sufficient to create thermal necrosis. As previously discussed, varying the electrode 24a,b size and spacing can control the size and shape of irreversible electroporation induced necrotic zone 65a. Electric pulse amplitude and length can be varied to control the size and shape of the thermally induced necrotic zones near the tissue-electrode-interface. In other embodiments, the electrical ablation device 800 comprising multiple needle electrodes 824a-m may be used to treat the undesirable tissue 48 located on the surface of the liver 50, for example.

Figure 5:
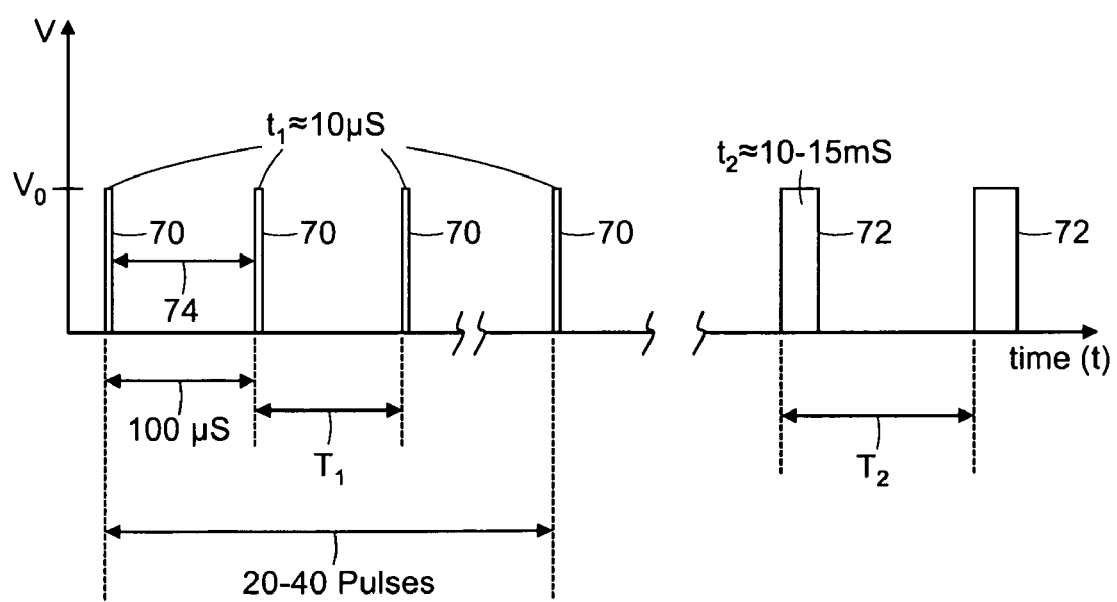
FIG. 5 is a graphical representation of a series of electrical pulses that may be applied to undesirable tissue to create a first necrotic zone by inducing irreversible electroporation in the tissue and to create a second necrotic zone by inducing thermal effects near the electrode-tissue-interface using the electrical ablation system shown in FIG. 4.

FIG. 5 is a graphical representation of a series of electrical pulses that may be applied to undesirable tissue to create a first necrotic zone by inducing irreversible electroporation in the tissue and to create a second necrotic zone by inducing thermal effects near the electrode-tissue-interface using the electrical ablation system 10 shown in FIG. 4. Time (t) is shown along the horizontal axis and voltage (VDC) is shown along the vertical axis. Initially the undesirable tissue 48 is exposed to a first series of electrical pulses 70 of a first predetermined amplitude, length, and frequency sufficient to induce the irreversible electroporation necrotic zone 65a. Subsequently, the undesirable tissue near the electrode-tissue-interface is exposed to a second series of electrical pulses 72 of a second predetermined amplitude, length, and frequency sufficient to induce thermal necrotic effects on the tissue and create thermal necrotic zones 63a,b. As shown in FIG. 5, the first series of pulses 70 comprises about 20 to 40 electric pulses having an amplitude of about 1000 VDC, pulse length $t_1$ of about 10 µs to about 15 µs, and a period $T_1$ (e.g., pulse repetition rate $f_1=1/T_1$) of about 10 µs ($f_1=10000$ Hz). The first series of pulses is sufficient to induce irreversible electroporation in the necrotic zone 65a. The period $T_1$ is defined as the pulse length $t_1$ plus the pulse spacing 74, e.g., the time between a falling edge of a pulse and a rising edge of a subsequent pulse. The second series of pulses 72 may comprises a single pulse or multiple pulses having an amplitude of about 500 VDC, pulse length $t_2$ of about 10 ms to about 15 ms, and a period $T_2$ of about 100 ms ($f_2=10$ Hz). The second series of pulses is sufficient to create thermal necrotic zones 63a,b in the tissue near the electrode-tissue-interface immediately surrounding the respective electrodes 24a,b. In one embodiment, $f_1=f_2=10$ Hz (i.e., $T_1=T_2=100$ ms).

In one embodiment, the thermal necrotic zones 63a,b formed in the tissue immediately surrounding the electrodes 24a,b at the tissue-electrode-interface are beneficial to stop bleeding in the undesirable tissue 48 as a result of the mechanical trauma resulting from inserting or embedding the electrodes 24a,b into the undesirable tissue 48 of the liver 50. Although in general irreversible electroporation induced by electric pulses do not cause thermal necrosis or other detrimental thermal effects, the longer electrical pulses 72 may be applied to the undesirable tissue 48 in succession to thermally seal the tissue immediately surrounding the electrodes 24a,b at the tissue-electrode-interface. Thus, the technique of applying a combination of a first series of substantially shorter electrical pulses 70 (in the microseconds range) and a second series of substantially longer energy pulses 72 (in the milliseconds range) may be employed for sealing vessels prior to transecting a vessel. Accordingly, the first series of pulses 70 may be applied to a vessel to induce cell necrosis by irreversible electroporation. Then, the second series of pulses 72 may be applied to vessel to create thermal necrotic zones to seal the vessel prior to dissecting the vessel.

In various embodiments, a series of electrical pulses may be characterized according to the following parameters as may be provided by the energy source 14, for example. In one embodiment, the energy source 14 may be configured to produce DC electric pulses at frequencies in the range of about 1 Hz to about 10000 Hz, amplitudes in the range of about ±100 to about ±3000 VDC, and pulse lengths (e.g., pulse width, pulse duration) in the range of about 1 µs to about 100 ms. The polarity of the electric potentials coupled to the electrodes 24a,b may be reversed during the electrical ablation therapy. For example, initially, the DC electric pulses may have a positive polarity and an amplitude in the range of about +100 to about +3000 VDC. Subsequently, the polarity of the DC electric pulses may be reversed such that the amplitude is in the range of about −100 to about −3000 VDC. In one embodiment, the undesirable cells in the tissue treatment region may be electrically ablated with DC pulses suitable to induce irreversible electroporation at frequencies of about 10 Hz to about 100 Hz, amplitudes in the range of about +700 to about +1500 VDC, and pulse lengths of about 10 µs to about 50 µs. In another embodiment, the abnormal cells in the tissue treatment region may be electrically ablated with an electrical waveform having an amplitude of about +500 VDC and pulse duration of about 20 ms delivered at a pulse period T or repetition rate, frequency f=1/T, of about 10 Hz.

FIGS. 6, 7, and 8 illustrate one embodiment of an electrical ablation device 290 to treat undesirable tissue located within body lumen using electrical energy. FIG. 6 illustrates a sectioned view of one embodiment of the electrical ablation device 290. FIG. 7 illustrates an end view of the embodiment of the electrical ablation device 290 shown in FIG. 6. FIG. 8 illustrates a cross-sectional view of the embodiment of the electrical ablation device 290 shown in FIG. 6. As previously discussed, reflux disease of the greater saphenous vein (GSV) can result in a varicose vessel 292, which is illustrated in FIG. 8. Conventionally, varicose veins have been treated by stripping and then applying either chemical or thermal ablation to internal portions of a lumen defined by the varicose vessel 292. In the embodiment illustrated in FIGS. 6-8, the electrical ablation device 290 is configured to couple to the energy source 14 and to be inserted within a lumen defined by the varicose vessel 292. Once inserted into the varicose vessel 292, the electrical ablation device 290 may be energized by the energy source 14 to apply high-voltage DC electrical pulses to an inner wall 294 portion of the varicose vessel 292. High-voltage DC pulses may be used to ablate the undesirable tissue and to subsequently seal the varicose vessel 292. The embodiment illustrated in FIGS. 6-8, however, is not limited in this context, and the electrical ablation device 290 may be employed to treat and seal tissue within any inner body lumen using energy in the form of electrical pulses supplied by the energy source 14.

Referring to FIGS. 6-8, the electrical ablation device 290 comprises a probe 296 comprising a cannula, channel, or lumen 300 extending longitudinally therethrough. The distal end 298 of the probe 296 comprises first and second ring electrodes 302a,b to which a potential difference may be applied by the energy source 14. The first and second ring electrodes 302a,b may be coupled to respective positive and negative terminals of the energy source 14 through corresponding first and second electrical conductors 304a,b. The first and second electrical conductors 304a,b extend through respective conduits 306a,b formed within the probe 296 and extend longitudinally therethrough. The first and second electrical conductors 304a,b may be electrically coupled to the first and second ring electrodes 302a,b in any suitable manner. The first and second ring electrodes 302a,b are adapted to receive energy in the form of electrical pulses from the energy source 14. The electrical pulses generate an electric field suitable for treating, e.g., ablating, the undesirable tissue within a lumen such as the lumen defined by the varicose vessel 292 as shown in FIG. 8. In one embodiment, once energized by the energy source 14, the first and second ring electrodes 302a,b generate an electric field suitable to induce irreversible electroporation in the undesirable tissue. It will be appreciated that a potential difference may be created across the first and second ring electrodes 302a,b to generate an electric field strength suitable to induce irreversible electroporation in the undesirable tissue. In other embodiments, the probe 296 may comprise one or more electrodes in addition to the first and second ring electrodes 302a,b.

The electrical ablation probe 296 has a form factor that is suitable to be inserted within a lumen defined by the varicose vessel 292 and to ablate tissue in the tapered lumen 298 portion of the varicose vessel 292. The probe 296 engages the inner wall 294 of the varicose vessel 292 in the tapered lumen 298 portion of the varicose vessel 292. Suction 306 applied at a proximal end of the probe 296 draws a vacuum within the lumen 300 of the probe 296 to collapse the varicose vessel 292 at the distal end 298 of the probe 296. Once the vessel 292 is collapsed or pulled down by the suction 306, a first pulse train 302 of high-voltage DC electrical pulses at a first amplitude $A_1$ (e.g., ~1000V amplitude) and a first pulse length $T_1$ (e.g., ~50 microseconds) is applied to the first and second ring electrodes 302a,b by the energy source 14. The high-voltage DC pulse train 302 eventually kills the cells within the tapered lumen 298 portion of the varicose vessel 292 by irreversible electroporation. A second pulse train 304 having a lower voltage amplitude $A_2$ (e.g., ~500 VDC) and a second longer pulse length $T_2$ (e.g., ~15 milliseconds) is applied to the first and second ring electrodes 302a,b of the probe 296 to thermally seal the varicose vessel 292. As previously discussed, in one embodiment, the polarity of the electrical pulses may be inverted or reversed by the energy source 14 during the abla-tion or sealing treatment process. In various embodiments, the electrical pulses may be characterized by the parameters in accordance with the output of the energy source 14 as discussed with respect to FIGS. 1 and 5, for example.

FIG. 9 illustrates one embodiment of an electrical ablation system 400 in use to treat non-metastatic prostate cancer in a patient. As previously discussed, a radical prostatectomy in which the entire prostate 404 and surrounding lymph nodes are removed is one of the conventional treatments for prostate cancer. Like most other forms of cancer, radiation therapy may be used in conjunction with or as an alternate method for the treatment of prostate cancer. Another thermal ablation technique for the treatment of prostate cancer is RF interstitial tumor ablation (RITA) via trans-rectal ultrasound guidance. While these conventional methods for the treatment of prostate cancer are effective, they are not preferred by many surgeons and may result in detrimental thermal effects to healthy tissue surrounding the prostate. The electrical ablation system 400 in accordance with the described embodiments provides improved electrical ablation of prostate cancer using irreversible electroporation pulses through supplied by an energy source to electrodes positioned into and/or proximate the prostrate cancer tissue.

With reference to FIG. 9, the electrical ablation system 400 comprises an electrical ablation device 402 comprising at least two electrodes 402a,b, and the energy source 14. The electrical ablation system 400 may be adapted for use in conjunction with the electrical ablation system 10 described in FIG. 1. The electrodes 402a,b are configured to be positioned within internal body lumens or cavities and, in one embodiment, may be configured for use in conjunction with the flexible endoscope 12 also described in FIG. 1. The electrodes 402a,b are configured to couple to the corresponding electrical conductors 18a,b, the handpiece 16, the activation switch 62, and the energy source 14, as previously discussed in FIG. 1. The first electrode 402a comprises a wire or flexible conductive tube that may be introduced through the urethra 406 into the prostate 404 proximally to the bladder 410. The first electrode 402a may be located into the prostate 404 using well known fluoroscopy or ultrasonic guidance, for example. The second electrode 402b comprises a pad and may be introduced into the anus 408 and advanced to a location proximate to the prostate 404. The first electrode 402a has a much smaller surface area relative to the trans-anally placed second electrode 402b pad. The first electrode 402a may be connected to the positive (+) terminal of the energy source 14 and the second electrode 402b may be connected to the negative (−) terminal of the energy source 14. In one embodiment, the energy source 14 may e configured as a high-voltage DC electric pulse generator. The activation switch 62 portion of the handpiece 16, as shown in FIG. 1, can be used to energize the electrical ablation system 400 to ablate the non-metastatic cancer in the prostate 404 by irreversible electroporation pulses supplied by the energy source 14 and delivered through the electrodes 402a,b as described in FIG. 10 below. In other embodiments, the probe 296 may comprise one or more electrodes in addition to the first and second electrodes 402a,b.

FIG. 10 is a graphical representation of a series of electrical pulses 412 that may be applied to undesirable tissue to induce irreversible electroporation suitable to ablate non-metastatic cancer of the prostrate 404 as described in FIG. 9. Time (t) is shown along the horizontal axis and voltage (V) is shown along the vertical axis. A series of electrical pulses 412 having a predetermined amplitude $V_o$ and pulse length to sufficient to induce irreversible electroporation may be applied to the prostate 404 through the electrodes 402a,b to ablate the undesirable cancerous tissue. Multiple electrical pulses 412, for example, 20 to 40 pulses, of amplitude of about 1500 to about 3000 volts DC ($V_o$) each having a pulse length to of about 10 µs to about 50 µs, and a period (T) of about 10 ms. The electrical pulses 412 having such parameters are sufficient to induce irreversible electroporation to ablate the cancerous tissue in the prostate 404. The period T (e.g., pulse repetition rate f=1/T) may be defined as the pulse length to plus the length of time between pulses, or the pulse spacing 414. A conductive fluid may be introduced into the urethra 406 to extend the range of the positive electrode 402a. In various embodiments, the electrical pulses may be characterized by the parameters in accordance with the output of the energy source 14 as discussed with respect to FIGS. 1 and 5, for example.

FIG. 11 illustrates one embodiment of the electrical ablation system 10 described FIG. 1 in use to treat basal cell carcinoma (BCC) tissue. In FIG. 11, the electrical ablation system 10, described in FIG. 1, is shown in use to treat BCC tissue 502. BCC tissue 502 is a slowly growing cutaneous malignancy derived from a rapidly proliferating basal layer of the epidermis 504. As previously discussed, conventional treatments for BCC include surgical excision, cryo-therapy, radiation, photodynamic therapy, Moh's micrographic surgery, and topical treatments with 5-fluorouracil. Minimally-invasive methods of treating BCC include laser ablation with a pulsed carbon dioxide laser. Although, the treatment of BCC with a carbon dioxide laser has been shown to be effective on tumors ranging in size from about 5 mm to about 40 mm, carbon dioxide treatment is a thermal method of treating tissue that may cause permanent thermal damage to healthy tissue surrounding the BCC tissue and requires costly capital investment in carbon dioxide laser equipment.

The electrical ablation device 20 of the electrical ablation system 10 may be used to induce irreversible electroporation suitable to treat undesirable BCC tissue using electrical pulses supplied by the energy source 14. The first and second electrodes 24a,b are transcutaneously inserted through the epidermis 504 and embedded into the BCC tissue 502. The first and second electrodes 24a,b are separated by a distance "D." The first electrode 24a is electrically to the positive (+) output of the energy source 14 and the second electrode 24b is electrically connected to the negative (−) output of the energy source 14. In one embodiment, the energy source 14 may be a high-voltage DC generator. The energized the electrodes 24a,b generate an electric field inducing irreversible electroporation suitable for ablating the undesirable BCC tissue 502 located between the electrodes 24a,b. A larger portion of the BCC tissue 502 may be ablated by relocating and re-energizing the first and second electrodes 24a,b using the technique previously described with reference to FIG. 3, for example. As previously discussed, varying the electrode 24a,b size and spacing can control the size and shape of irreversible electroporation induced necrotic zone. Accordingly, as previously discussed, increasing the electrode 24a,b diameter and spacing between the electrodes 24a,b enables the generation of an electric field over a much larger tissue regions and thus the ablation of larger volumes of undesirable tissue. In other embodiments, the electrical ablation device 800 comprising multiple needle electrodes 824a-m may be used to treat the BCC tissue 502, for example.

FIG. 12 is a graphical representation of a series of electrical pulses 512 that may be applied to undesirable tissue to induce irreversible electroporation suitable to ablate BCC tissue as described in FIG. 11. Time (t) is shown along the horizontal axis and voltage (V) is shown along the vertical axis. As shown in FIG. 12, a series of electrical pulses 512 having a predetermined amplitude $V_o$ and pulse length $t_o$ sufficient to induce irreversible electroporation may be applied to the BCC tissue 502 to ablate the undesirable cancerous tissue. About 20 to about 40 pulses 512 of with an amplitude of about 1500 to about 3000 VDC ($V_o$), a pulse length $t_o$ of about 10 µs to about 50 µs, a period T (the pulse length $t_o$ plus the pulse spacing 54) of about 10 ms may be suitable for inducing irreversible electroporation to ablate the undesirable BCC tissue 502 in the region D between the electrodes 24a,b. Multiple placements of the electrode 24a,b in rapid succession and the application of additional pulses 512 can be used to ablate larger portions of the BCC tissue 502, as previously discussed in FIG. 3. As previously discussed, varying the electrode 24a,b size and spacing can control the size and shape of irreversible electroporation induced necrotic zone. Accordingly, increasing the electrode 24a,b diameter and spacing the electrodes 24a,b further apart (e.g., greater than "D") enables the generation of an electric field over a much larger tissue regions and thus the ablation of larger volumes of undesirable tissue. Injecting a conductive fluid into the BCC tissue 502 is another technique to increase the size and shape of the irreversible electroporation induced necrotic zone and extend the range of the positive electrode 24a, for example. In various embodiments, the electrical pulses may be characterized by the parameters in accordance with the output of the energy source 14 as discussed with respect to FIGS. 1 and 5, for example.

FIG. 13A illustrates one embodiment of an electrical ablation device 600 in a collapsed state. The electrical ablation device 600 has a configuration suitable for the treatment of undesirable tissue located in a lumen, abscess, void, or cavity. Although other electrode configurations may be effective for treating line-of-sight regions of tissue, such electrodes may not be as effective at treating tissue within a cavity. To overcome these limitations, the electrical ablation device 600 comprises an electrode configured to inflate and expand into the cavity to make contact with tissue along the inner wall of the cavity. The electrical ablation device 600 comprises an elongate tubular body extending from a proximal end to a distal end. In one embodiment, the electrical ablation device 600 may comprise a conductive elastomer electrode 602 portion (e.g., balloon, tip) and a non-conductive catheter 604 portion, which may be formed of a non-electrically conductive (e.g., electrically insulative) elastomeric material. The electrical ablation device 600 may be referred to as a balloon catheter, balloon probe, or balloon-tipped catheter, for example, without limitation. In one embodiment, the inflatable portion of the conductive elastomer electrode 602 may be formed of an electrically conductive elastomer suitable for coupling to the energy source 14 via an electrically conductive terminal 610 and a first electrically conductive wire 608a. Once inflated, the elastomeric properties of the conductive elastomer electrode 602 conform to the internal walls of the cavity. Upon energizing, the conductive elastomer electrode 602 delivers electrical pulses to the tissue within the internal walls of the cavity to induce irreversible electroporation.

In one embodiment, the electrical ablation device 600 may be fabricated using a concurrent injection process such that the conductive elastomer electrode 602 portion and the non-conductive catheter 604 portion are formally integrally. In another embodiment, the electrical ablation device 600 may be fabricated by manufacturing the conductive elastomer electrode 602 and the non-conductive catheter 604 separately and then joining the two components using any suitable joining method such as, for example, bolting, screwing, welding, crimping, gluing, bonding, brazing, soldering, press fitting, riveting, heat shrinking, heat welding, ultrasonic welding, or any other suitable method.

FIG. 13B illustrates one embodiment of the electrical ablation device 600 shown in FIG. 13A in an inflated state. As previously discussed, in an inflated state the conductive elastomer electrode 602 may be employed for ablating cancerous tumors growing within internal body lumens such as the esophagus or the large bowel, or in cavities remaining when cancerous tumors are removed from solid tissue, such as the breast. Although surgical resection of tumors in solid tissue can include a margin of healthy tissue, cancer cells may remain in the tissue within the cavity. The conductive elastomer electrode 602 may be inserted in the cavity, inflated, and energized by the energy source 14 to expose the tissue within the cavity to electrical pulses suitable to induce irreversible electroporation to ablate any cancer cells remaining within the cavity.

FIG. 14 is a cross-sectional view of the electrical ablation device 600 showing a cross-sectional view of the conductive elastomer electrode 602 and the non-conductive catheter 604 shown in FIGS. 13A and 13B. The conductive elastomer electrode 602 may be coupled to a first end 606 of the electrically conductive wire 608a. The wire 608a may be located through the non-conductive catheter 604 and the first end 606 electrically connected (e.g., bonded, soldered, brazed) to the conductive elastomer electrode 602 through the electrically conductive terminal 610. In one embodiment, the non-conductive catheter 604 may be extruded with an embedded strip of conductive material serving as the electrically conductive terminal 610. The wire 608a may be electrically connected to one end of the electrically conductive terminal 610. In one embodiment, the electrical ablation device 600 may be configured to couple to one terminal of the energy source 14 via a second end of the electrically conductive wire 608a. A return electrode 612 (e.g., in the form of a pad or needle electrode) is coupled to a second electrically conductive wire 608b, which is coupled to another terminal of the energy source 14. The return electrode 612 may be orientated proximal to the conductive elastomer electrode 602 of the electrical ablation device 600 (e.g., the balloon catheter). When irreversible electroporation energy pulses are applied to the conductive elastomer electrode 602 of the electrical ablation device 600, the tissue between the conductive elastomer portion 602 and the return electrode 608b is ablated, e.g., destroyed by the pulsed irreversible electroporation energy. In other embodiments, the return electrode 612 may comprise multiple electrodes, for example.

In one embodiment, the conductive elastomer electrode 602 may be fabricated from or may comprise an electrically conductive material suitable for conducting electrical energy from the energy source 14 to the internal cavity sufficient tot induce irreversible electroporation to the tissue within the cavity. The electrically conductive elastomer material is similar to conductive elastomers used as gasket material for electronic enclosures used for shielding electronic devices from electromagnetic interference (EMI). Conductive elastomers may be formed by infiltrating an elastomeric matrix with electrically conductive filler materials such as silver, gold, copper, or aluminum, to produce a hybrid material having the elastic properties of the elastomeric matrix and the electrically conductive properties of the metallic filler materials (some materials may have volume resistivity values as low as 0.004 Ω-cm, for example). The conductive elastomer may be formed as thin sheets, catheters, and balloons suitable for medical applications. In one embodiment, the conductive elastomer electrode 602 may be fabricated from medical grade polyurethane material comprising at least one electrically conductive coating on an outer surface thereof. In another embodiment, the conductive elastomer electrode 602 may be made from an electrically conductive material. In yet another embodiment, the conductive elastomer electrode 602 may be made from an electrically insulative material, such as the medical grade polyurethane, and inflated with a conductive fluid (e.g., saline) to form the electrically conductive portion of the conductive elastomer electrode 602.

In one embodiment the conductive elastomer electrode 602 may be coupled to the anode (+) electrode of the energy source 14 and in another embodiment the conductive elastomer electrode 602 may be coupled to the cathode (−) electrode of the energy source 14. It will be appreciated that the polarity of the conductive elastomer electrode 602 may be reversed by reversing the output polarity of the energy source 14. In one embodiment, the conductive elastomer electrode 602 may be coupled to either the anode (+) or the cathode (−) of the energy source 14. For example, the conductive elastomer electrode 602 may be coupled to the cathode (+) of the energy source 14 relative to a ground plane cathode (−) in contact with the patient and coupled to the negative terminal of the energy source 14.

FIG. 15 illustrates one embodiment of the electrical ablation device shown in FIG. 13A inserted through the mouth and esophagus to ablate cancerous tissue in the esophagus using electrical pulses. As shown in FIG. 15, a hollow outer sleeve 620 or trocar is inserted into the upper gastrointestinal tract of a patient and receives a flexible endoscopic portion of an endoscope 622 (e.g., gastroscope), similar to the endoscope 12 described in FIG. 1. A variety of different types of endoscopes are known and, therefore, their specific construction and operation will not be discussed in great detail herein. In various embodiments, the flexible endoscopic portion 620 may be fabricated from nylon or high-density polyethylene plastic, for example. FIG. 15 illustrates, in general form, one embodiment of the electrical ablation device 600 that can be inserted through a natural orifice such as the mouth 626 and advanced through a cavity or lumen such as the esophagus 628, e.g., esophageal cavity, to apply electrical pulses sufficient to induce irreversible electroporation to ablate the undesirable cancerous tissue 630 located in the esophagus 628.

FIG. 16 illustrates the distal portion 624 of the endoscope 622 shown in FIG. 15. As shown in FIG. 16, the electrical ablation device 600 is advanced through the distal end 624 of the endoscope 622. In various embodiments, the endoscope 622 can serve to define various tool-receiving passages 628, or "working channels," that extend from the natural orifice 626 to the surgical site. In addition, the endoscope 622 comprises a viewing port 630. The endoscope 622 may be used for viewing the surgical site within the patient's body. Various cameras and/or lighting apparatuses may be inserted into the viewing port 630 of the endoscope 622 to provide the surgeon with a view of the surgical site.

With reference now to FIGS. 15 and 16, the electrical ablation device 600 is one of the tools or surgical instruments that can be accommodated in the tool-receiving passage 628 of the endoscope 622. The conductive elastomer electrode 602 (e.g., balloon, tip) and the non-conductive catheter 604 are configured to communicate with at least one pressurized air source 634 and a vacuum source 632 to respectively inflate and deflate the conductive elastomer electrode 602. In one embodiment, a vacuum/air tube 636 can be sized to receive other surgical instruments therein. In various embodiments, the endoscope 622 may comprise a video camera that communicates with a video display unit 638 that can be viewed by the surgeon during the operation. In addition, the endoscope

622 may further comprise a fluid-supply lumen therethrough that is coupled to an inflation fluid such as a water source 640, saline solution, and/or any other suitable inflation fluid and/or an air supply lumen that is coupled to the air source 642. In various embodiments, the fluid-supply lumen, e.g., the inflation fluid line, may be coupled to conventional inline valves (not shown) to control the flow of inflation fluid. For example, a proximal end of the inline valve may be removably coupled to a conventional inflation syringe. The fluid-supply lumen defines an inflation lumen that fluidically communicates with the interior of the conductive elastomer electrode 602 (e.g., the balloon electrode) via an aperture (not shown). The fluid-supply lumen provides a fluid communication path for inflating the conductive elastomer electrode 602 with a conductive fluid. The fluid may be either saline or air or other suitable electrically conductive inflation fluid. As previously discussed, the conductive elastomer electrode 602 is coupled to the energy source 14 to delivers electrical pulses to the esophageal cavity. The transcutaneous electrode 612 is also coupled to the energy source 14 through electrically conductive wire 608*b*.

In use, the electrical ablation device 600 may be introduced into a natural orifice such as the mouth 626 and advanced into a lumen, abscess, void, or cavity such as the esophagus 628, as shown in FIG. 15. In the illustrated embodiment, the conductive elastomer electrode 602 is inserted through the working channel 628 of the endoscope 622 and into the lumen or cavity defined by the esophagus 628 and the return electrode 612 is inserted transcutaneously and is located proximate to the cancerous tissue 630. Once located within the esophagus 628, the conductive elastomer electrode 602 may be inflated using either the water source 640 or the air source 642. The water source 640 may supply a conductive solution (e.g., saline solution) to enhance the conductivity of the conductive elastomer electrode 602 and to enhance the contact area between the conductive elastomer electrode 602 and the inner wall of the esophageal cavity 628 including the cancerous tissue 630. Once inflated, the conductive elastomer electrode 602 is energized by the energy source 14 with a number of high-voltage DC electrical pulses to cause necrosis of the undesirable the cancerous tissue 630 between the conductive elastomer electrode 602 and the return electrode 612. In this example, the high-voltage DC electrical pulses generate an electric field in a concentric zone around the esophageal cavity 628. The electric field has a sufficient magnitude and pulse length to induce irreversible electroporation in the undesirable cancerous tissue 630. The depth of the necrotic zone depends on the amplitude of the applied electric field, the pulse length, the number of pulses, and the repetition rate or frequency of the pulses. In various embodiments, the electrical pulses may be characterized by the parameters in accordance with the output of the energy source 14 as discussed with respect to FIGS. 1 and 5, for example.

FIGS. 17-20 illustrate a method of treating residual undesirable tissue within cavities formed in the solid tissue after removal of a mass of undesirable tissue. FIG. 17 illustrates a cross-sectional view of a breast 702 showing a cavity 700 that may be left after a lumpectomy to remove a tumor from the breast 702. In tumors that grow in solid tissue, the rate of recurrence of undesirable tissue depends on the margin of healthy tissue relative to the undesirable tissue that is removed. Accordingly, to minimize the recurrence of the tumor once the undesirable tissue is removed from the breast 702, the residual tissue in the cavity 700 should be ablated. The residual tissue may be ablated using the techniques previously described in FIGS. 13-16 above or the techniques described in FIGS. 18-20 below.

FIG. 18 illustrates one embodiment of a catheter 704 inserted into the cavity 700 left in the breast 702 after a lumpectomy procedure. A distal end 706 of the catheter 704 comprises a compressed sponge 708 or any suitable type of expandable foam material. A sleeve 710 slidably disposed over the catheter 704 and the sponge 708 contains the sponge 708 until it is ready to expand into the cavity 700. When the sleeve 710 is retracted in the direction indicated by arrow 712, the sponge 708 may be expanded into the cavity 700 by pumping saline into the sponge 708 through the catheter 704. An electrode 714 is inserted through the catheter 704 and into the sponge 708 such that the electrode 714 is in electrical communication with the sponge 708. The electrode 714 may be coupled to the positive terminal of the energy source 14, for example.

FIG. 19 illustrates an expanded sponge filling the cavity 700 left in the breast 702 following a lumpectomy as shown in FIG. 17. As shown in FIG. 19, the sponge 708 has been soaked with saline solution and has expanded to fill the cavity 700 upon removal of the sleeve 710. Multiple wire electrodes 714 may be embedded in the saline soaked sponge 708. Each of these wire electrodes 714 may be coupled to the positive terminal of the energy source 14. The body or outer portion of the breast 702 may be electrically grounded through one or more large surface area electrodes 716*a,b*. It will be appreciated that in other embodiments that either a single surface area electrode or more than two surface area electrodes may be employed, without limitation. The negative electrodes 716*a,b* are connected to the negative terminal of the energy source 14. The sponge 708 and the residual tissue within the cavity 700 are exposed to a series of electric pulses (e.g., high-voltage DC electric pulses) suitable for inducing irreversible electroporation. The high-voltage DC electric pulses in the form graphically illustrated in FIG. 5, 10, or 12 generate an electric field sufficient to cause apoptosis/necrosis in a zone extending beyond the edge of the cavity 700, for example. In various embodiments, the electrical pulses may be characterized by the parameters in accordance with the output of the energy source 14 as discussed with respect to FIGS. 1 and 5, for example.

FIG. 20 illustrates the expanded sponge 708 intact to fill the cavity 700 left in the breast 702 as shown in FIG. 17 following irreversible electroporation ablation therapy. After the irreversible electroporation ablation treatment is completed, the positive electrode 714 is removed from the cavity 700 and the negative electrodes 716*a,b* are removed from the breast 702. The sponge 708, however, may be left inside to fill the cavity 700.

FIG. 21 illustrates a mesh of a finite element model 709 of a sponge inserted in the cavity 700 left in the breast 702 as shown in FIG. 17. The horizontal and the vertical axes represent distance in meters (m) with the center defined at (0,0). As shown in FIG. 21, the mesh of the finite element model 709 is a two-dimensional representation of the sponge similar to the sponge 708 inserted in the cavity 700 of the breast 702 previously described in FIGS. 17-20, for example.

FIG. 22 is a graphical representation of electric potential and electrical field strength sufficient to induce irreversible electroporation when applied to the sponge 708 located within the breast cavity 700 as shown in FIG. 17. The horizontal and the vertical axes represent distance in meters (m) with the center defined at (0,0). As shown in FIG. 22, electric field strength in Volts/meter (V/m) is represented by electric field lines 718 shown as concentric contours or circles extending from an outer perimeter of the sponge 708 to a point in space 726 where the electric field strength is at a minimum. A scale 722 to the right of the graph represents electric field strength in V/m. Electric potential 720 in Volts (V) applied to the sponge 708 within the cavity 700 is represented by the shaded zones 720. A vertical scale 724 shown to the right of the electric field strength scale 722 represents electric potential in V with the minimum potential at the bottom and the maximum potential at the top. The electrical field lines 718*a,b* just outside the outer perimeter of the sponge 708 are representative of an electric field potential 720*a* of about 1400 to about 2000 V sufficient to cause cell necrosis by irreversible electroporation.

FIG. 23 is a graphical representation of electric field strength contours in volts per meter (V/m) developed when electrodes are energized by an energy source. The horizontal and the vertical axes represent distance in meters (m) with the center defined at (0,0). FIG. 23 illustrates a graph 730 of electric field strength contours developed when the electrodes 24*a,b* are inserted into the sponge 708 and energized by the energy source 14, as described in FIGS. 17-22. A vertical scale 732 shown to the right of the graph 730 represents the electric field strength in a range from a minimum of about 50,000V/m (bottom) to a maximum of about 100,000V/m (top). Irreversible electroporation energy in this range of electric field strength (e.g., about 50,000V/m to about 100,000V/m) are suitable for efficient and effective treatment of medical conditions that require the ablation of undesirable tissue from a localized region (i.e., in the case of the treatment of cancer). With reference to the embodiment described in FIGS. 17-22, needle-probes or electrodes 24*a,b* are inserted into the sponge 708. As shown in the graph 730, electric field strength contours 734, 736 represent the maximum electric field strength (e.g., about 80,000 to about 100,000V/m) in a region proximate to the location where the needle electrodes 24*a,b* are inserted into the sponge 708. Electric field strength contour 738 represents electric field strength of about 50,000V/m. In regions outside the sponge 708, the electric field strength peaks at contour 742 to about 100,000V/m and then tapers off with distance to about 80,000V/m at contour 744 to about 50,000V/m at contour 746. It will be appreciated that other electric field strength contours may be developed to render effective irreversible electroporation ablation therapy. Accordingly, the embodiments described herein should not be limited in this context.

The embodiments of the electrical ablation devices described herein may be introduced inside a patient using minimally invasive or open surgical techniques. In some instances it may be advantageous to introduce the electrical ablation devices inside the patient using a combination of minimally invasive and open surgical techniques. Minimally invasive techniques provide more accurate and effective access to the treatment region for diagnostic and treatment procedures. To reach internal treatment regions within the patient, the electrical ablation devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Surgical devices, such as an electrical ablation devices, may be introduced to the treatment region through the working channels of the endoscope to perform key surgical activities (KSA), including, for example, electrical ablation of tissues using irreversible electroporation energy. Some portions of the electrical ablation devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina). A rigid endoscope may be introduced via trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Once an electrical ablation device is inserted in the human body internal organs may be reached using trans-organ or translumenal surgical procedures. The electrical ablation device may be advanced to the treatment site using endoscopic translumenal access techniques to perforate a lumen, and then, advance the electrical ablation device and the endoscope into the peritoneal cavity. Translumenal access procedures for perforating a lumen wall, inserting, and advancing an endoscope therethrough, and pneumoperitoneum devices for insufflating the peritoneal cavity and closing or suturing the perforated lumen wall are well known. During a translumenal access procedure, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A guidewire is then feed through the endoscope and is passed through the puncture in the stomach wall and into the peritoneal cavity. The needle knife is removed, leaving the guidewire as a placeholder. A balloon catheter is then passed over the guidewire and through the working channel of the endoscope to position the balloon within the opening in the stomach wall. The balloon can then be inflated to increase the size of the opening, thereby enabling the endoscope to push against the rear of the balloon and to be feed through the opening and into the peritoneal cavity. Once the endoscope is positioned within the peritoneal cavity, numerous procedures can be performed through the working channel of the endoscope.

The endoscope may be connected to a video camera (single chip or multiple chips) and may be attached to a fiber-optic cable system connected to a "cold" light source (halogen or xenon), to illuminate the operative field. The video camera provides a direct line-of-sight view of the treatment region. The abdomen is usually insufflated with carbon dioxide ($CO_2$) gas to create a working and viewing space. The abdomen is essentially blown up like a balloon (insufflated), elevating the abdominal wall above the internal organs like a dome. $CO_2$ gas is used because it is common to the human body and can be removed by the respiratory system if it is absorbed through tissue.

Once the electrical ablation devices are located at the target site, the diseased tissue may be electrically ablated or destroyed using the various embodiments of electrodes discussed herein. The placement and location of the electrodes can be important for effective and efficient electrical ablation therapy. For example, the electrodes may be positioned proximal to a treatment region (e.g., target site or worksite) either endoscopically or transcutaneously (percutaneously). In some implementations, it may be necessary to introduce the electrodes inside the patient using a combination of endoscopic, transcutaneous, and/or open techniques. The electrodes may be introduced to the tissue treatment region through a working channel of the endoscope, an overtube, or a trocar and, in some implementations, may be introduced through percutaneously or through small—keyhole—incisions.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. An electrical ablation apparatus, comprising:
a shaft;
first and second selectably deployable electrodes slideably receivable within the shaft, each electrode comprising a first end configured to couple to an energy source and a second end configured to couple to a tissue treatment region, wherein the first selectably deployable electrode is deployable independent of the second selectably deployable electrode and the second selectably deployable electrode is deployable independent of the first selectably deployable electrode;
a sheath slideably coupled to the first and second electrodes, the sheath slideable with respect to the first and second electrodes and the shaft, the sheath is disposable in a first position and a second position, the first position covers the first and second electrodes in a deployed state and the second position exposes the first and second electrodes in a deployed state; and
an energy source coupled to the first and second selectably deployable electrodes, the energy source configured to deliver a first series of electrical pulses sufficient to induce cell necrosis by irreversible electroporation and a second series of electrical pulses sufficient to induce cell necrosis by thermal heating, through at least one of the first and second selectably deployable electrodes;
wherein the first series of electrical pulses is characterized by a first amplitude, a first pulse length, and a first frequency; and
wherein the second series of electrical pulses is characterized by a second amplitude, a second pulse length, and a second frequency.

2. The electrical ablation apparatus of claim 1, wherein the first amplitude is about 1000 VDC, the first pulse length is about 10 µs to about 15 µs, and the first frequency is about 10 Hz; and wherein the second amplitude is about 500 VDC, the second pulse length is about 10 ms to about 15 ms, and the second frequency is about 10 Hz.

3. The electrical ablation apparatus of claim 1, wherein the first amplitude is selected in the range of about +100 to about +3000 VDC, the first pulse length is selected in the range of about 1 µs to about 100 ms, and the first period is selected in the range of about 1 Hz to about 10000 Hz.

4. The electrical ablation apparatus of claim 1, wherein the first series of electrical pulses comprises about 20 to about 40 pulses and the second series of electrical pulses comprises at least one pulse.

5. The electrical ablation apparatus of claim 1, wherein the first and second electrodes are needle electrodes each having a diameter in the range of about 0.5 mm to about 1.5 mm and are separated by a distance of about 5.0 mm to about 10.0 mm.

6. The electrical ablation apparatus of claim 5, wherein the first series of electrical pulses is sufficient to create a first necrotic zone in a first portion of tissue induced by irreversible electroporation in an area surrounding both the first and second electrodes and wherein the second series of electrical pulses is sufficient to create a second necrotic zones in a second portion of tissue induced by thermal heating in an area near the electrode-tissue-interface.

7. The electrical ablation apparatus of claim 6, wherein the first series of electrical pulses is sufficient to ablate basal cell carcinoma tissue.

8. The electrical ablation apparatus of claim 6, wherein the first series of electrical pulses is sufficient to ablate prostrate cancer tissue.

9. The electrical ablation apparatus of claim 1, wherein the first and second electrodes are ring electrodes.

10. The electrical ablation apparatus of claim 9, wherein the first series of electrical pulses is sufficient to create a first necrotic zone in a first portion of tissue induced by irreversible electroporation in a body lumen and wherein the second series of electrical pulses is sufficient to create a second necrotic zones in the body lumen by thermal heating to seal the body lumen.

11. The electrical ablation apparatus of claim 10, wherein the first series of pulses is sufficient to ablate varicose vein tissue resulting from reflux disease of the greater saphenous vein.

12. The electrical ablation apparatus of claim 1, wherein the first electrode comprises a plurality of electrodes.

13. The electrical ablation apparatus of claim 1, wherein the second electrode comprises a plurality of electrodes.

14. The electrical ablation apparatus of claim 1, wherein:
the first selectably deployable electrode may be retracted to allow the electrical ablation apparatus to pivot about a pivot point defined by the second selectably deployable electrode; and
the second selectably deployable electrode may be retracted to allow the electrical ablation apparatus to pivot about a point defined by the first selectably deployable electrode.

* * * * *